United States Patent
Birnir et al.

(10) Patent No.: US 12,161,695 B2
(45) Date of Patent: Dec. 10, 2024

(54) GABA A RECEPTOR AGONISTS FOR TREATMENT OF DISORDERS INFLUENCED BY DYSFUNCTION BETA CELLS

(71) Applicant: DIAMYD MEDICAL AB, Stockholm (SE)

(72) Inventors: Bryndis Birnir, Stockholm (SE); Ulf Hannelius, Stockholm (SE); Anton Lindqvist, Stockholm (SE)

(73) Assignee: DIAMYD MEDICAL AB, Stockholm (SE)

( * ) Notice: Subject to any disclaimer, the term of this patent is extended or adjusted under 35 U.S.C. 154(b) by 146 days.

(21) Appl. No.: 16/971,645

(22) PCT Filed: Feb. 21, 2019

(86) PCT No.: PCT/EP2019/054364
§ 371 (c)(1),
(2) Date: Aug. 20, 2020

(87) PCT Pub. No.: WO2019/162403
PCT Pub. Date: Aug. 29, 2019

(65) Prior Publication Data
US 2020/0384086 A1    Dec. 10, 2020

(30) Foreign Application Priority Data

Feb. 22, 2018 (SE) .................................. 1850201-3
Mar. 9, 2018 (SE) .................................. 1850259-1

(51) Int. Cl.
| | | |
|---|---|---|
| *A61P 3/10* | (2006.01) | |
| *A61K 31/05* | (2006.01) | |
| *A61K 31/197* | (2006.01) | |
| *A61K 31/515* | (2006.01) | |
| *A61K 31/5513* | (2006.01) | |
| *A61K 38/26* | (2006.01) | |
| *A61K 45/06* | (2006.01) | |

(52) U.S. Cl.
CPC .............. *A61K 38/26* (2013.01); *A61K 31/05* (2013.01); *A61K 31/197* (2013.01); *A61K 31/515* (2013.01); *A61K 31/5513* (2013.01); *A61K 45/06* (2013.01); *A61P 3/10* (2018.01)

(58) Field of Classification Search
CPC .............................. A61K 31/5513; A61P 3/10
See application file for complete search history.

(56) References Cited

U.S. PATENT DOCUMENTS 9,089,531 B2 * 7/2015 Kaufman ............ A61K 39/0008
2010/0166675 A1 * 7/2010 Wang .................... C07K 14/605
514/561

FOREIGN PATENT DOCUMENTS

EE          03952        *  2/2003
WO    WO 2012/050907 A2   4/2012

OTHER PUBLICATIONS

Wan et al;, Diabetes, Metabolic Syndrome and Obesity: Targets and Therapy, 8:79-87, (2015).*
Braun et al., J. Gen. Physiol. 123:191-204,( 2004).*
Rorsman and Braun et al., Ann. Rev. Physiol. 75: 155-179, (2013 ).*
Lahtela et al., "Phenobarbital treatment enhances insulin mediated glucose metabolism in man", Research Communications in Chemical Pathology and Pharmacology, 1984, 44(2): 215-226.
Tian et al., "γ-Aminobutyric Acid Regulates Both the Survival and Replication of Human β-Cells", Diabetes, 2013, 62: 3760-3765.
Cuttitta et al., "Taurine's Effects on the Neuroendocrine Functions of Pancreatic β Cells", 2013, In: AEMB—Taurine, 775: 299-310.
Gu et al., "Suppressive Effect of GABA on Insulin Secretion from the Pancreatic Beta-Cells in the Rat", Life Sciences, 1992, 52: 687-694.
Dong et al., "Gamma-aminobutyric acid up- and downregulates insulin secretion from beta cells in concert with changes in glucose concentration", Diabetologia, 2006, 49: 697-705.
Braun et al., "γ-Aminobutyric Acid (GABA) Is an Autocrine Excitatory Transmitter in Human Pancreatic γ-Cells", Diabetes, 2010, 59: 1694-1701.
Caumo et al., "First-phase insulin secretion: does it exist in real life? Considerations on shape and function", Am J Physiol Endocrinol Metab, 2004, 287: E371-E385.
Fehse et al., "Exenatide Augments First- and Second-Phase Insulin Secretion in Response to Intravenous Glucose in Subjects with Type 2 Diabetes", The Journal of Clinical Endocrinology & Metabolism, 2005, 90(11): 5991-5997.
Sosenko et al., "Acceleration of the Loss of the First-Phase Insulin Response During the Progression to Type 1 Diabetes in Diabetes Prevention Trial-Type 1 Participants", Diabetes, 2013, 62: 4179-4183.

* cited by examiner

*Primary Examiner* — Gyan Chandra
(74) *Attorney, Agent, or Firm* — James S. Keddie; Bozicevic, Field & Francis LLP

(57) ABSTRACT

The present invention relates to methods for treatment or prevention of disorders caused influenced by dysfunction of β cells by administering to said patient a compound selected from the group consisting of GABA$_A$ receptor agonists. The invention further relates to in vitro methods for finding potentially useful pharmaceutical compounds.

11 Claims, 12 Drawing Sheets

Specification includes a Sequence Listing.

Fig 1 a-c
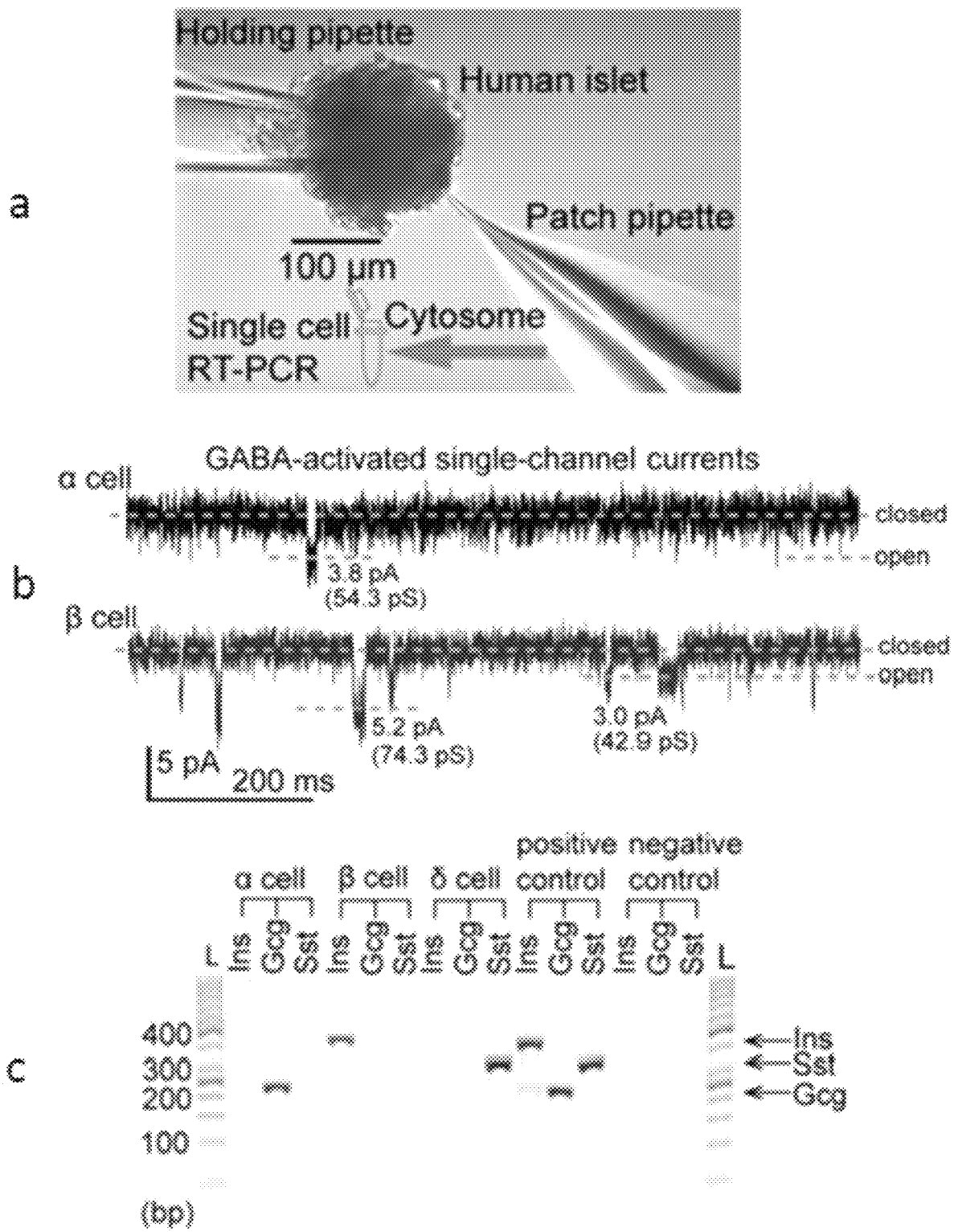

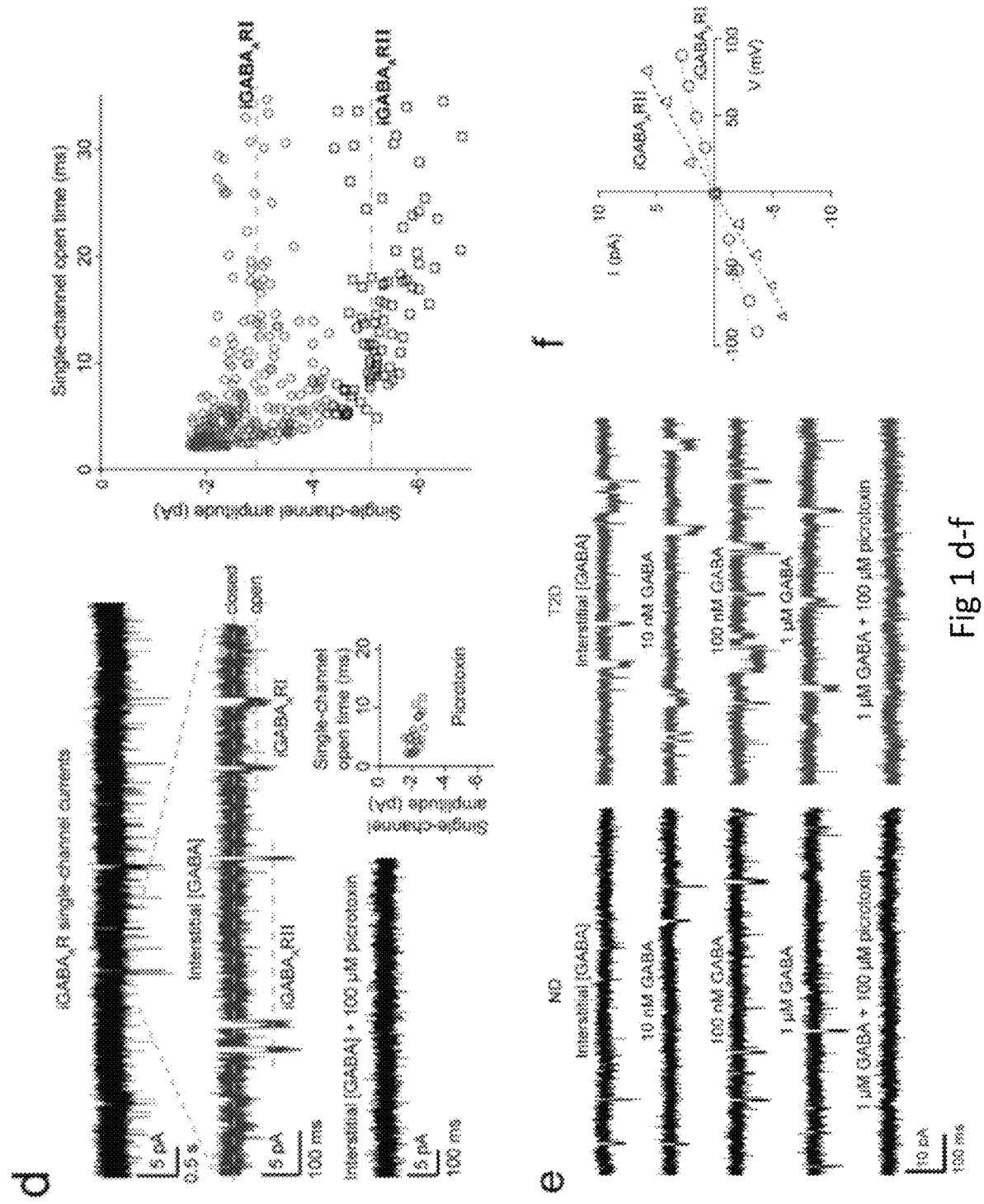
Fig 1 d-f

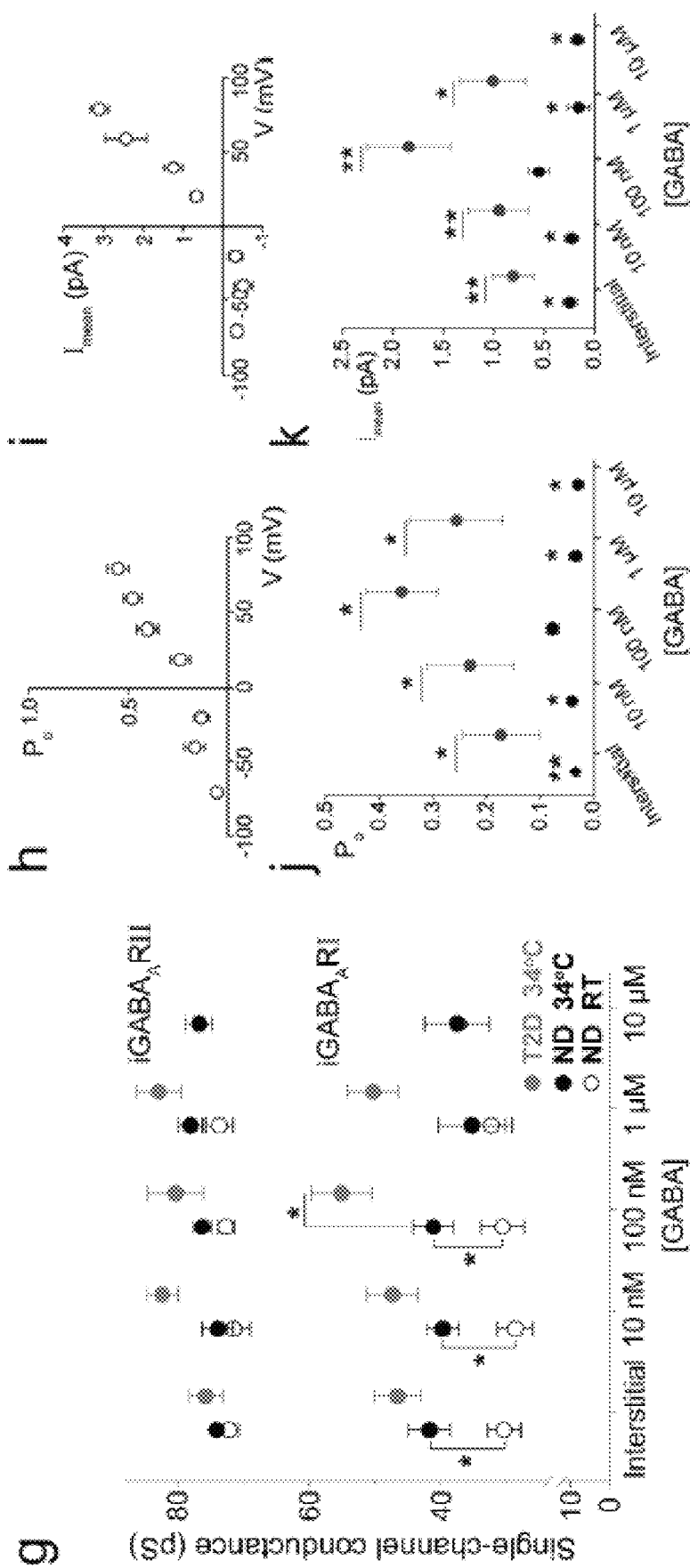
Fig 1 g-k

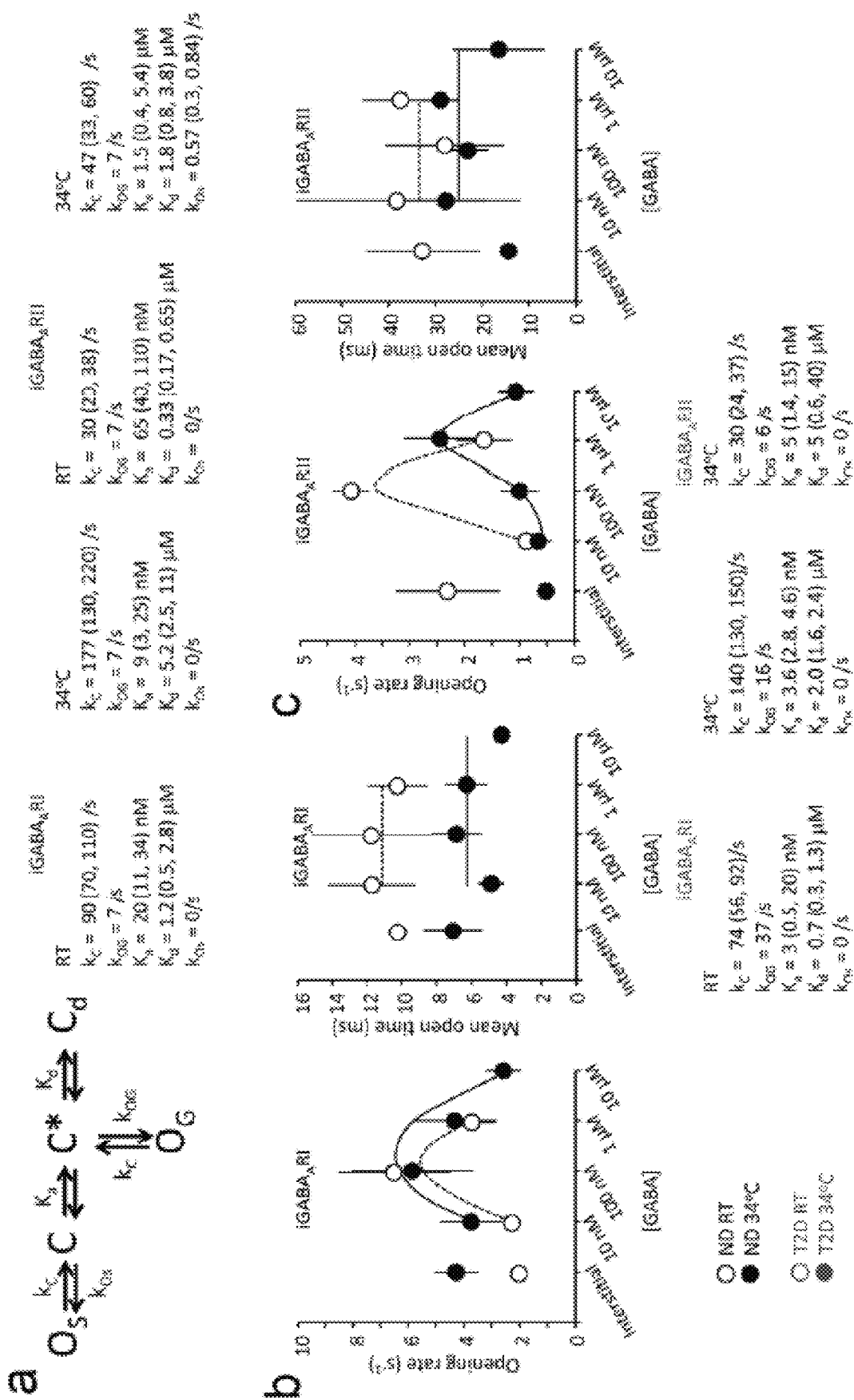
Fig 2 a-c

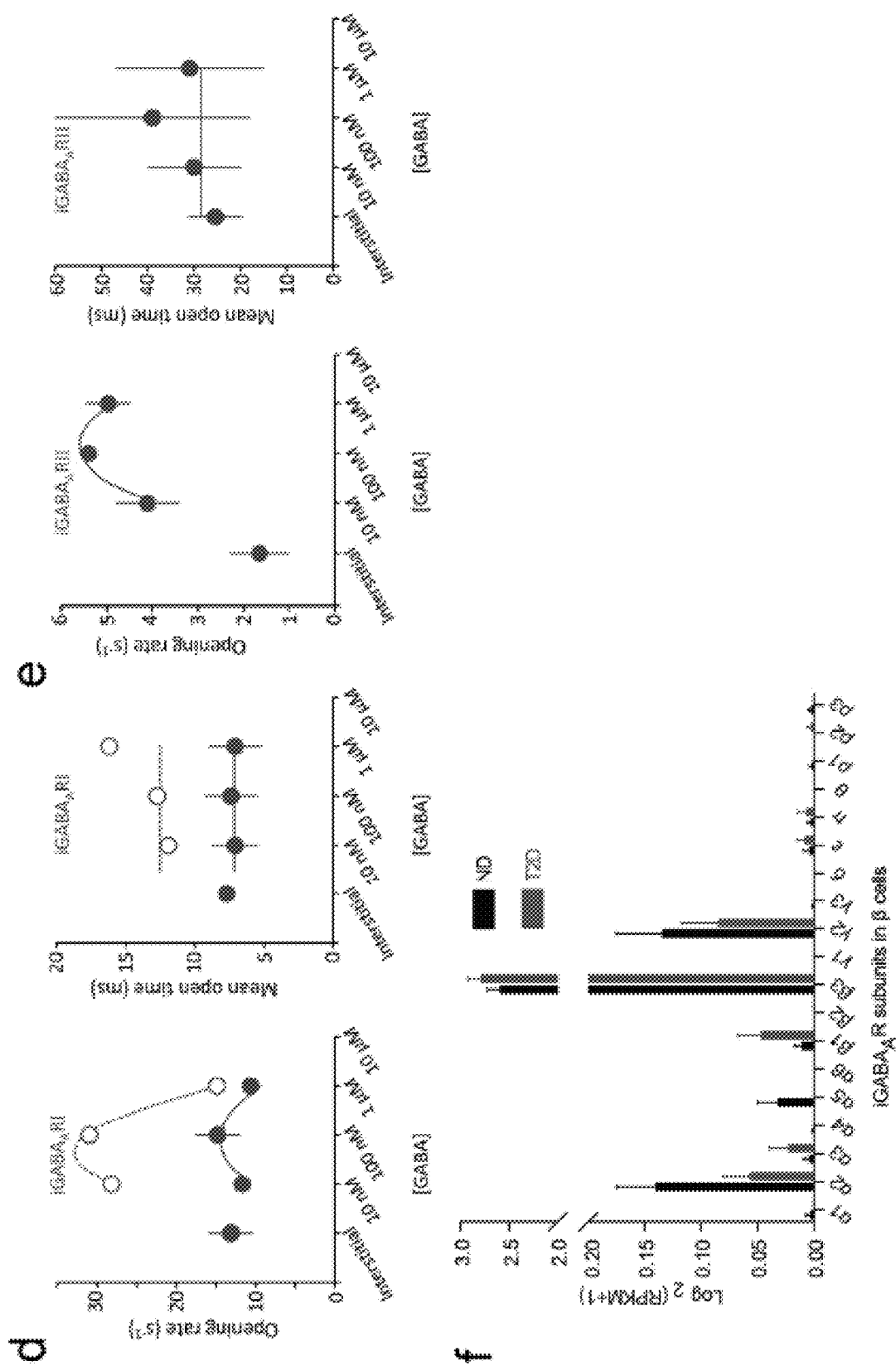
Fig 2 d-f

Fig 3 a-e
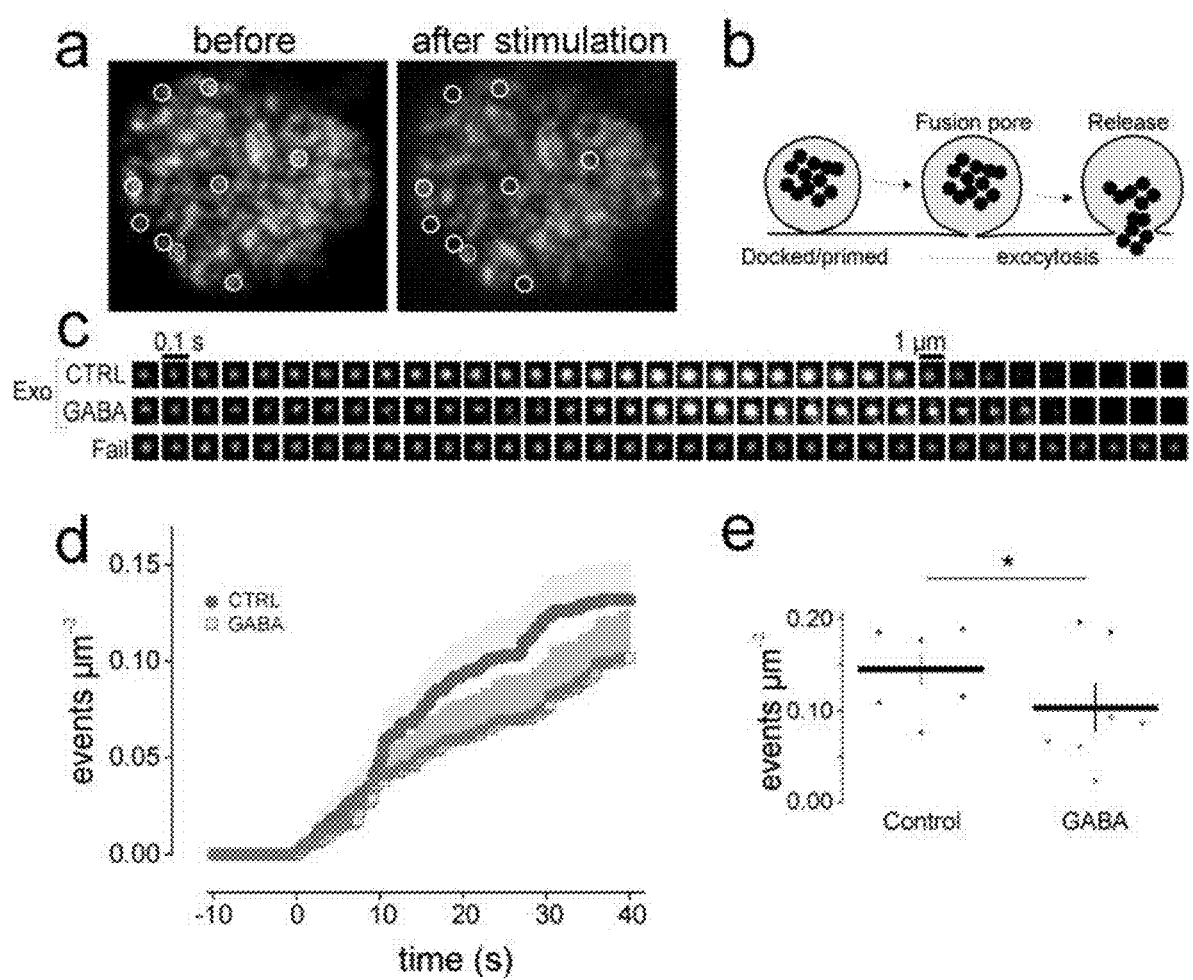

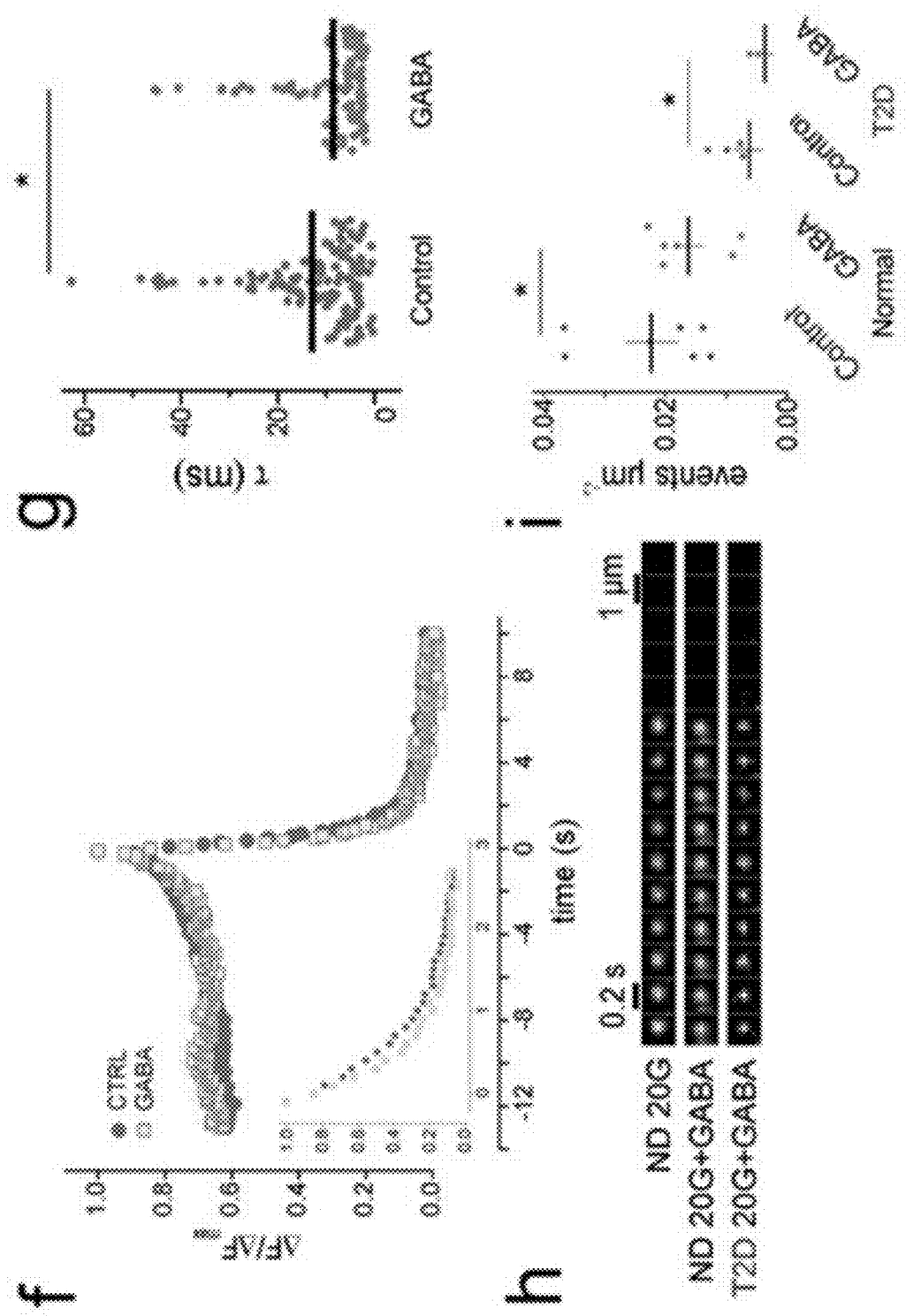
Fig 3 f-i

Fig 4 a
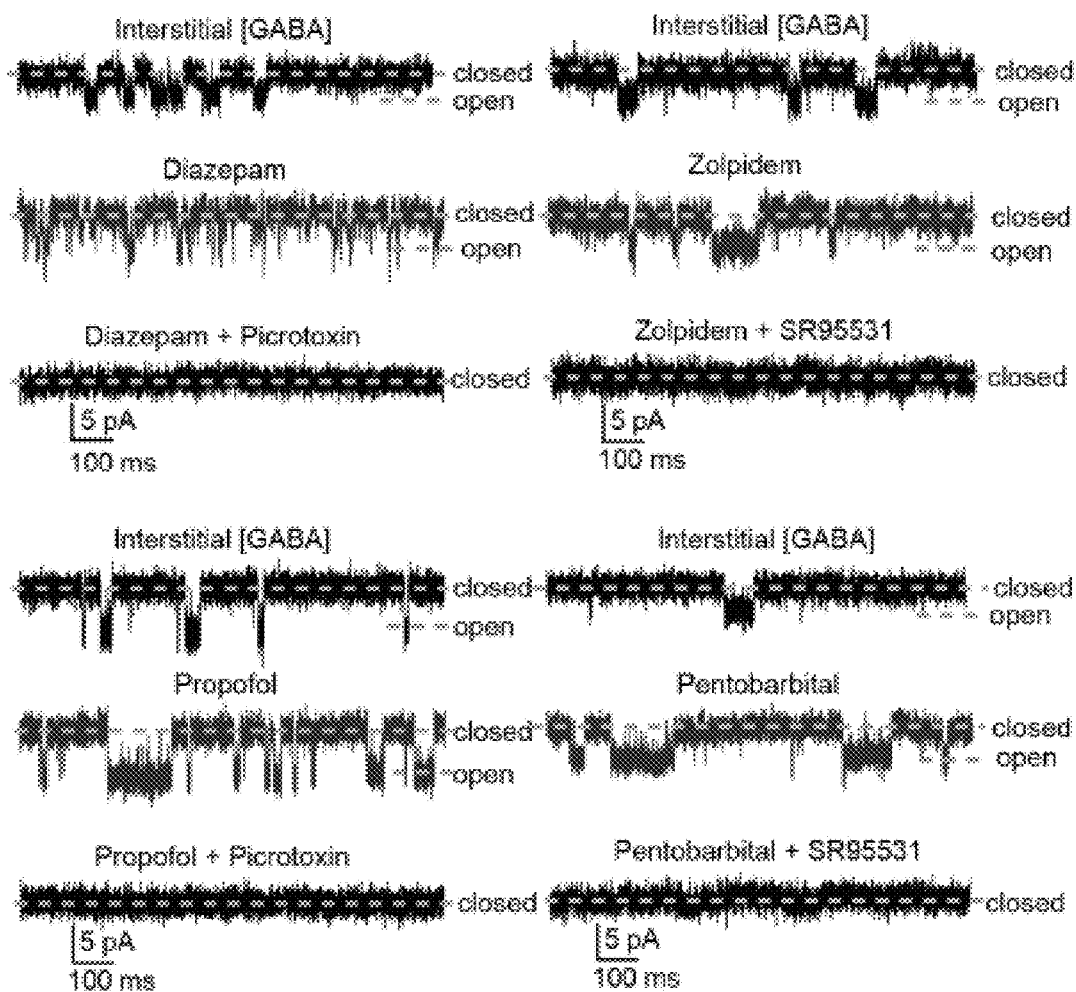
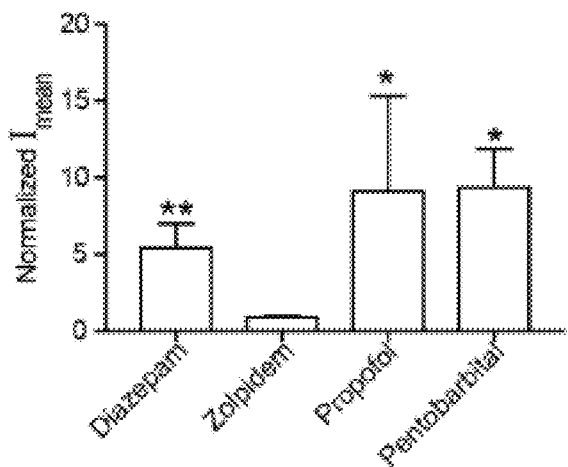
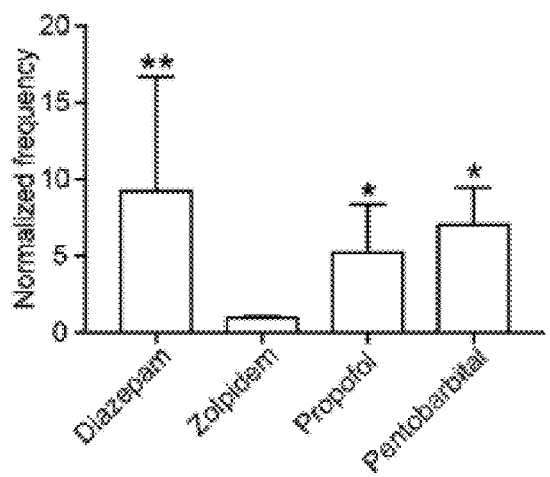

Fig 4 b
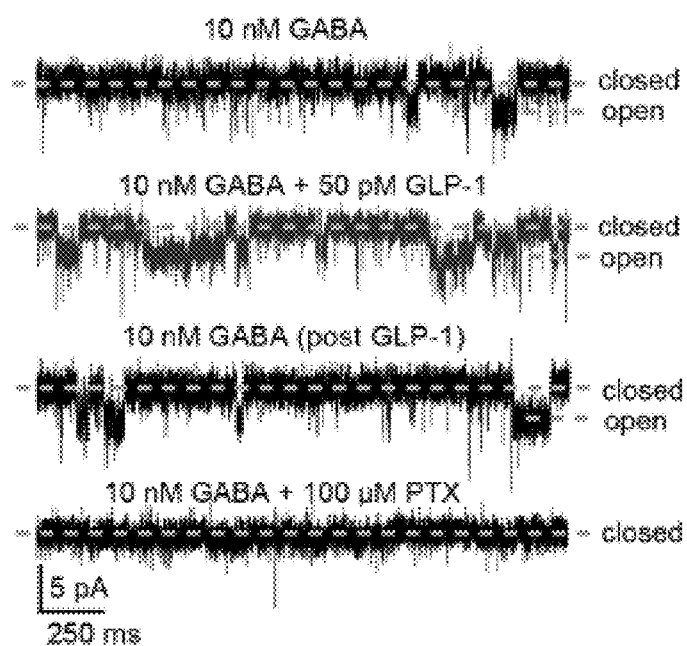
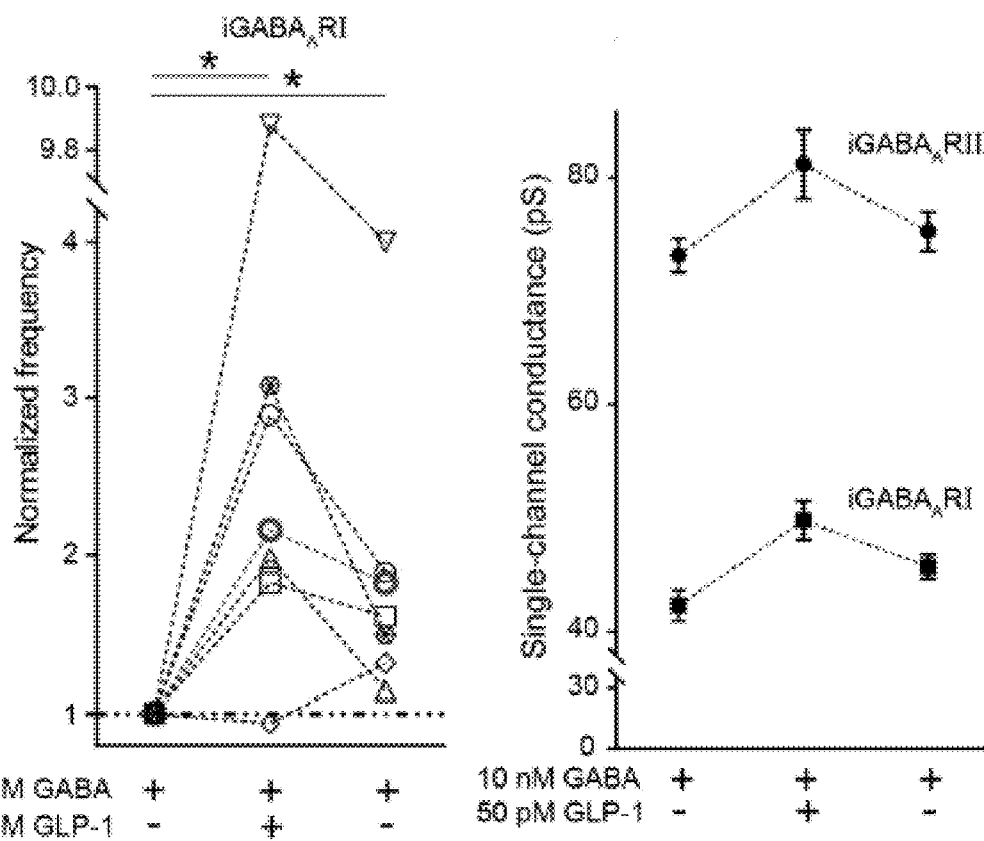

SEQUENCE LISTING

```
<160> NUMBER OF SEQ ID NOS: 12

<210> SEQ ID NO 1
<211> LENGTH: 24
<212> TYPE: DNA
<213> ORGANISM: artificial sequence
<220> FEATURE:
<223> OTHER INFORMATION: synthetic oligonucleotide

<400> SEQUENCE: 1
agaggccatc aagcagatca ctgt                                          24

<210> SEQ ID NO 2
<211> LENGTH: 20
<212> TYPE: DNA
<213> ORGANISM: artificial sequence
<220> FEATURE:
<223> OTHER INFORMATION: synthetic oligonucleotide

<400> SEQUENCE: 2
ctgcgggctg cgtctagttg                                               20

<210> SEQ ID NO 3
<211> LENGTH: 18
<212> TYPE: DNA
<213> ORGANISM: artificial sequence
<220> FEATURE:
<223> OTHER INFORMATION: synthetic oligonucleotide
```

```
<400> SEQUENCE: 3
ccatcaagca gatcactg                                                      18

<210> SEQ ID NO 4
<211> LENGTH: 19
<212> TYPE: DNA
<213> ORGANISM: artificial sequence
<220> FEATURE:
<223> OTHER INFORMATION: synthetic oligonuceotide

<400> SEQUENCE: 4
cactaggtag agagcttcc                                                     19

<210> SEQ ID NO 5
<211> LENGTH: 23
<212> TYPE: DNA
<213> ORGANISM: artificial sequence
<220> FEATURE:
<223> OTHER INFORMATION: synthetic oligonucleotide

<400> SEQUENCE: 5
aaggcgagat ttcccagaag agg                                                23

<210> SEQ ID NO 6
<211> LENGTH: 21
<212> TYPE: DNA
<213> ORGANISM: artificial sequence
<220> FEATURE:
<223> OTHER INFORMATION: synthetic oligonucleotide

<400> SEQUENCE: 6
acgtggctag caggtgatgt t                                                  21

<210> SEQ ID NO 7
<211> LENGTH: 21
<212> TYPE: DNA
<213> ORGANISM: artificial sequence
<220> FEATURE:
<223> OTHER INFORMATION: synthetic oligonucleotide

<400> SEQUENCE: 7
gcaacgttcc cttcaagaca c                                                  21

<210> SEQ ID NO 8
<211> LENGTH: 20
<212> TYPE: DNA
<213> ORGANISM: artificial sequence
<220> FEATURE:
<223> OTHER INFORMATION: synthetic oligonucleotide

<400> SEQUENCE: 8
actggtgaat gtgccctgtg                                                    20

<210> SEQ ID NO 9
<211> LENGTH: 21
<212> TYPE: DNA
<213> ORGANISM: artificial sequence
<220> FEATURE:
<223> OTHER INFORMATION: synthetic oligonucleotide

<400> SEQUENCE: 9
gctttaggag cgaggttcgg a                                                  21

<210> SEQ ID NO 10
<211> LENGTH: 21
```

```
<212> TYPE: DNA
<213> ORGANISM: artificial sequence
<220> FEATURE:
<223> OTHER INFORMATION: synthetic oligonucleotide

<400> SEQUENCE: 10
gggcatcatt ctccgtctgg t                                      21

<210> SEQ ID NO 11
<211> LENGTH: 20
<212> TYPE: DNA
<213> ORGANISM: artificial sequence
<220> FEATURE:
<223> OTHER INFORMATION: synthetic oligonucleotide

<400> SEQUENCE: 11
cccagactcc gtcagtttct                                        20

<210> SEQ ID NO 12
<211> LENGTH: 21
<212> TYPE: DNA
<213> ORGANISM: artificial sequence
<220> FEATURE:
<223> OTHER INFORMATION: synthetic oligonucleotide

<400> SEQUENCE: 12
aagtacttgg ccagttcctg c                                      21
```

GABA A RECEPTOR AGONISTS FOR TREATMENT OF DISORDERS INFLUENCED BY DYSFUNCTION BETA CELLS

CROSS-REFERENCE TO RELATED APPLICATIONS

This application is a § 371 national phase of International Application No. PCT/EP2019/054364, filed on Feb. 21, 2019, which claims the benefit of Swedish Application No. 1850201-3, filed on Feb. 22, 2018, and Swedish Application No. 1850259-1, filed on Mar. 9, 2018, all of which applications are incorporated by reference herein.

FIELD OF THE INVENTION

The present invention relates to methods of treatment of disorders involving malfunctioning Langerhans' islet cells and compounds useful in such treatments. The invention further relates to in vitro methods for finding potentially useful pharmaceutical compounds.

BACKGROUND

GABA is a signalling amino acid synthesized and released by the insulin secreting β cells in the pancreatic islets of Langerhans. In β cells, GABA is then stored in synaptic-like microvesicles, in the insulin granules and in the cytoplasm until secreted (Braun et al., 2010; Braun et al., 2004; Kanaani et al., 2015). The roles of GABA in the islets are many; GABA has been linked to regulation of β cells proliferation and β cell mass (Soltani et al., 2011; Tian et al., 2013), the change of α cells into β cells (Ben-Othman et al., 2017; Lawlor et al., 2017; Li et al., 2017), and regulation of hormone secretion (Braun et al., 2010; Li et al., 2015; Taneera et al., 2012). GABA also inhibits immune cells (Bjurstom et al., 2008; Tian et al., 2004) and, thereby, potentially increases β cells survival (Fiorina, 2013). Importantly, GAD autoantibodies are associated with the development of type 1 diabetes (T1D) where β cell mass decreases or even disappears whereas in T2D β cell function is compromised (American, 2017; Giorda et al., 2016) resulting in abnormally high blood glucose. What the physiologically relevant GABA concentrations are in the human islets or what GABA receptor subtypes participate in the signaling is not known (Caicedo, 2013; Rodriguez-Diaz and Caicedo, 2014; Rorsman and Braun, 2013). Importantly, in human islets, insulin-, glucagon- and somatostatin-secreting β, α and δ cells, respectively, all express GABAA receptors (Braun et al., 2010). This renders the human islet GABA signaling distinct from e.g. signaling in rat and guinea pig islets where functional $GABA_A$ receptors are not expressed in the β cells (Gilon et al., 1991; Jin et al., 2013; Rorsman et al., 1989; Wendt et al., 2004).

Although GABA has vital functions in the islets and, potentially, is protective in diabetes mellitus, little is known about the mechanisms of GABA signalling in human pancreatic islets. The islets are composed of clusters of specialised cells that respond to variations in the blood glucose levels by secreting hormones that maintain the glucose concentration in blood within the appropriate physiological range[12-14]. In type 2 diabetes, blood glucose is abnormally high whereas in type 1 diabetes, the control of blood glucose is lost, unless insulin is injected, due to disappearance of β cells from the islets.

The GABAA receptor activity in the brain is enhanced by a number of medicines such as the benzodiazepines, anesthetics and even by the metabolic hormone GLP-1 and its analogue exendin-4 (Korol et al., 2015; Olsen and Sieghart, 2008). GLP-1 is a very effective insulin secretagogue (Hoist, 2007). It is clearly of interest to understand the effects these compounds may have on the GABAA receptors in the human islet β cells.

GLP-1 (Glucagon like peptide 1) is a metabolic, gastro-intestinal hormone that plays an important role in maintaining body blood glucose levels. It is released upon ingestion of food, into the blood stream (Hoist J J 1994 Gastroenterology 107:1848-1855). GLP-1 stimulates the formation of GABA by the pancreatic β-cells (Ling, Z., et al., 2007, Am. J. Physiol. Endocrinol. Metab. 292: E1201-E1206). Furthermore, it has been shown that GLP-1 enhances pancreatic islet beta-cell neogenesis/proliferation and inhibits beta-cell apoptosis; in a glucose-dependent fashion (Nauck M A 2004 Horm Metab Res 36:852-858; Drucker D J 2001 Endocrinology 142:521-527).

SUMMARY OF THE INVENTION

In a first aspect, the invention relates to a method for treatment or prevention of disorders caused or influenced by dysfunction of β cells by decreasing the rate of insulin granule exocytosis in a human patient, said method comprising administering to said patient a compound selected from the group consisting of $GABA_A$ receptor agonists.

In a further aspect, the invention relates to a method for treatment or prevention of disorders caused or influenced by dysfunction of β cells by increasing the amount of insulin released per insulin granule exocytosis event in a human patient, said method comprising administering to said patient a compound selected from the group consisting of $GABA_A$ receptor agonists.

In a further aspect, the invention relates to a method for treatment or prevention of disorders caused or influenced by dysfunction of β cells by decreasing the rate of insulin granule exocytosis while increasing the amount of insulin released per insulin granule exocytosis event in a human patient, said method comprising administering to said patient a compound selected from the group consisting of $GABA_A$ receptor agonists.

In a further aspect, the invention relates to a method for ameliorating symptoms of a disorder caused or influenced by dysfunction of β cells, wherein said ameliorating of symptoms comprises decreasing the rate of insulin granule exocytosis in a patient by administering to said patient a compound selected from the group consisting of $GABA_A$ receptor agonists.

In further aspects, the invention relates to GABA and $GABA_A$ receptor agonists, for use in the above methods, as well as the use of GABA and $GABA_A$ receptor agonists in the manufacture of a pharmaceutical composition for use in a method according to the above.

In a further aspect, the invention relates to a method of treating Type 2 Diabetes in a human subject comprising administering a Positive Allosteric Modulator (PAM) of a GABA receptor for a period of time and in an amount effective to normalize the $GABA_A$ receptor subunit profile in said subject.

In a further aspect, the invention relates to a method for assessing therapeutic potential of a candidate compound, comprising administering the candidate compound to a subject having at least one $iGABA_AR$ supersensitive to GABA, for a period of time, and assessing whether the sensitivity to GABA has been decreased following said administration.

In a further aspect, the invention relates to a method for assessing therapeutic potential of a candidate compound, comprising measuring, in the presence of an iGABA$_A$R-agonist, the current through a iGABA$_A$R-molecule in the presence and absence, respectively, of said candidate compound wherein an increased current in the presence of the candidate compound indicates that candidate compound has a therapeutic potential.

In a further aspect, the invention relates to a method for assessing therapeutic potential of a candidate compound, comprising providing an islet cell from a diabetic donor and measuring the apparent affinity (Ka) for GABA of iGABA$_A$R-molecules in said cell in the presence and absence, respectively, of said candidate compound, wherein a higher apparent affinity in the presence of the candidate compound indicates that candidate compound has a therapeutic potential.

In a further aspect, the invention relates to a method for assessing therapeutic potential of a candidate compound, comprising providing an islet cell from a diabetic donor and measuring the opening frequency of iGABA$_A$R-molecules in said cell in the presence and absence, respectively, of said candidate compound, wherein an increased opening frequency in the presence of the candidate compound indicates that candidate compound has a therapeutic potential.

Preferred embodiments of the above mentioned aspects are discussed in the detailed description and set out in the appended claims.

DESCRIPTION OF THE DRAWINGS

FIG. 1. Characterization of GABA$_A$ receptor (iGABA$_A$R) single-channel currents in human pancreatic islet b cells. (a) Experimental set-up showing the process of single-channel current recording in intact human islet followed by single-cell RT-PCR. (b) Interstitial GABA-activated single-channel currents in α and β cells. Closed and open states of the single channels are marked with corresponding dash lines. Amplitudes of the currents (in pA) through and corresponding conductances (in pS) of the single channels are indicated. Vp=−70 mV for both cell. (c) Agarose gel showing islet hormone gene expression in single cells from intact islets. Ins, insulin; Gcg, glucagon; Sst, somatostatin; L, ladder; bp, base pair. (d) iGABA$_A$ single-channel currents, and currents at expanded time scale identifying two types of iGABA$_A$R, iGABA$_A$RI and II. Scatter plots of iGABA$_A$R single-channel current amplitudes versus their open times show two populations of iGABA$_A$Rs in a β cell. GABA$_A$R antagonist picrotoxin inhibited iGABA$_A$Rs (lowest panel). (e) iGABA$_A$ single-channel currents in a b cell activated first by interstitial GABA and then by sequentially applied GABA concentrations (10-1000 nM) to the islet from ND or T2D donor. The currents were then inhibited by picrotoxin. Vp=−70 mV, 34° C. and scale bars are common for the current recordings. (f) Current-voltage relationships for iGABA$_A$Rs at room temperature (RT). (g) Single-channel conductance of iGABA$_A$RI and II as a function of GABA concentration ([GABA]) in islets from ND (black symbols) and T2D (grey symbols) donors at RT (open symbols) and 34° C. (filled symbols). Data are mean±SEM from 3-11 cells. Unpaired Student's t-test, *P<0.05. (h and i) Open probability (Po) of and mean current ('mean) through the iGABAARs as a function of the membrane potential at 34° C. Data are mean±SEM from 4-10 cells. (j and k) Po of and absolute 'mean through iGABA$_A$Rs as a function of [GABA] for ND (black symbols) and T2D donors (grey symbols). Data from 3-8 cells at 34° C., Vp=−70 mV. Unpaired Student's t-test for intergroup comparisons and one-way ANOVA multiple comparisons versus control group (100 nM GABA) with Bonferroni post hoc test within ND group; *P<0.05, **P<0.01. SEM is shown if the range is larger than the symbol.

FIG. 2: Kinetic modeling of iGABA$_A$RI and II and expression pattern of iGABA$_A$R subunits in β cells. (a) A kinetic model describing iGABAAR channel behavior in the pancreatic islet b cells. (b and c) Fitting the kinetic model from (a) (curves) to the opening rate and mean open time (To) of iGABA$_A$RI and iGABA$_A$RII from ND donors at RT (n=7 and n=4, respectively) and at 34° C. (n=8 and n=8, respectively). (d and e) Corresponding opening rate and mean open time (To) for iGABA$_A$RI and iGABA$_A$RII from T2D donors and fit of the model in (a) to the data at RT (n=1) and at 34° C. (n=3). (f) Expression pattern of iGABA$_A$R subunits in single β cells from ND and T2D donors. The expression level was expressed as log2(RPKM+1) and data were presented as mean±SEM. RPKM, reads per kilobase of transcript per million mapped reads.

FIG. 3. Effect of GABA on insulin-granule exocytosis in human islets. (a) TIRF image showing labeled granules in a cell before and after application of 75 mM K$^+$. (b) Diagram of docked and primed insulin granules undergoing exocytosis. (c) Single insulin granule exocytotic events from islet cells were triggered by addition of 75 mM K$^+$. The cells expressed NPY-Venus as a granule label in the absence (CTRL) and presence of 100 nM GABA. Fail, non-responding granule which failed to undergo exocytosis. (d) Cumulative number of events per area in the presence and absence of GABA. (e) Analysis of (d) showed significantly decreased number of events per area in the presence of GABA. (f) Average fluorescence intensity and decay of granule fluorescence (inset) from 7 cells per condition in the presence and absence of GABA. (g) The decay constant τ was significantly larger (slower fluorescence decay) in control cells. (h) Single insulin granule exocytotic events from islet cells expressing NPY-mCherry under indicated conditions. 20G, 20 mM glucose. (i) Cumulative number of events per area under indicated conditions. *P<0.05.

FIG. 4. The modulation of iGABA$_A$R mediated single-channel currents in β cells by GABA$_A$R modulators and GLP-1. (a) Top: iGABA$_A$R-mediated single-channel currents recorded from islet β cells were enhanced by diazepam (1 μM), propofol (10 μM) and pentobarbital (100 μM) but not zolpidem (200 nM). Picrotoxin (100 μM) and SR95531 (100 μM) inhibited the iGABA$_A$R currents. Lower panel: Diazepam (n=5), propofol (n=4) and pentobarbital (n=4) but not zolpidem (n=4) significantly increased the mean single-channel current (Imean) and opening frequency of iGABA$_A$Rs (*P<0.05; **P<0.01, Mann-Whitney test). Data were presented as mean±SEM. (b) Top: iGABA$_A$R-mediated single-channel currents recorded from a β cell were potentiated by GLP-1 (50 pM) in the presence of GABA (10 nM). The enhanced channel activity was maintained after GLP-1 washout (post GLP-1) and picrotoxin (PTX; 100 μM) inhibited the currents. Lower panel: The opening frequency of iGABA$_A$RI channels was significantly increased by GLP-1 and after GLP-1 washout it remained significantly higher than that before GLP-1 application (*P<0.05, n=6). Each cell is identified by a specific symbol and connected by dashed lines (black, ND; grey, T2D). One-way ANOVA multiple comparisons versus control group (before GLP-1 application; Dunn's method). The application of GLP-1 and the following washout did not significantly change the single-channel conductance of either iGABA$_A$RI or iGABA$_A$RII (n=5). Data were presented as mean±SEM.

DEFINITIONS

Figure 5:
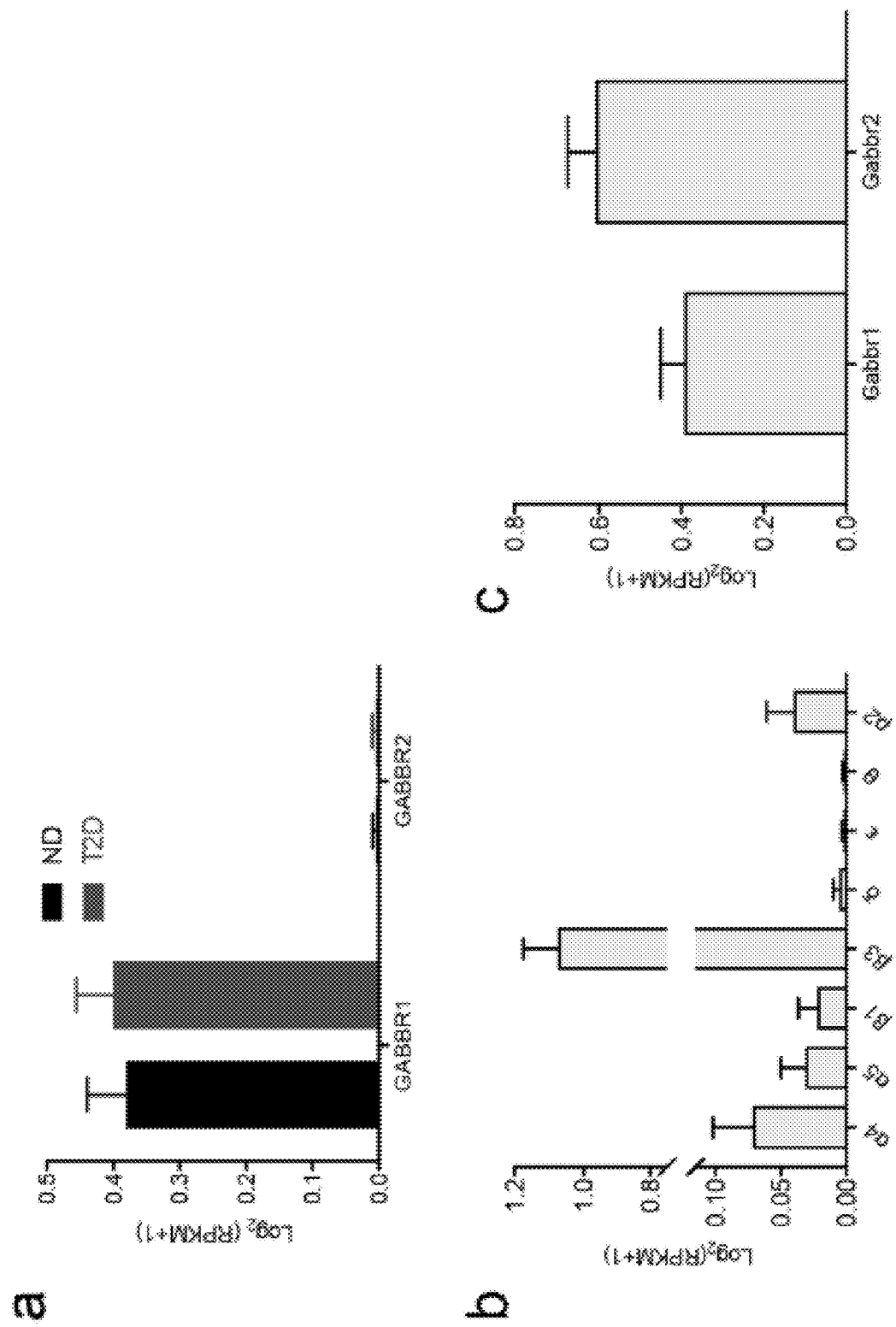
FIG. 5: The expression of GABAAR and GABABR subunit mRNA in human and mouse pancreatic islet β cells analyzed by single-cell RNAseq. (a) GABABR subunit expression from two published human islet single cell RNAseq data sets (single β cells, n=376 from ND donors, n=395 from T2D donors) (GEO: GSE81608 and ArrayExpress: E-MTAB-5060). (b) GABAAR subunit expression in single β cells (n=313) from male C57BL/6 mice (3-7 month of age) (GEO: GSE77980). (c) GABABR subunit expression in single β cells (n=313) from male C57BL/6 mice (3-7 month of age) (GEO: GSE77980). The expression level was calculated as log2 (RPKM+1) and data were presented as mean±SEM. RPKM, reads per kilobase of transcript per million mapped reads.

The term "$GABA_A$ receptor agonist" refers generally, as used herein, to a compound that directly enhances the activity of a $GABA_A$ receptor relative to the activity of the $GABA_A$ receptor in the absence of the compound. "$GABA_A$ receptor agonists" useful in the invention described herein include compounds such as GABA, muscimol, thiomuscimol, cis-aminocrotonic acid (CACA), homotaurine, bamaluzole, gabamide, GABOB, gaboxadol, ibotenic acid, isoguvacine, isonipecotic acid, phenibut, picamilon, progabide, quisqualamine, progabide acid (SL 75102).

The term "$iGABA_A$ Receptor", or "$iGABA_AR$" refers to a $iGABA_A$ receptor molecule as identified herein. The receptors are termed the receptor subtype, islet $iGABA_A$-receptor type-I, ($iGABA_AR$-I), and type-II, ($iGABA_AR$-II). The $iGABA_AR$-I is defined by an average conductance of 35 Pico Siemens (pS) (range $iGABA_AR$-I). The $iGABA_AR$-II is defined by a higher conductance with average of 70 pS activated by 10 nM GABA at room temperature. The critical border level is 55 pS at room temperature. At 34° C. the conductance is higher with average conductance of the channels of 40 pS for $iGABA_AR$-I and 85 pS for $iGABA_AR$-II. The critical border is at 60 pS.

The term "GLP-1" or "GLP-1 agonist" refers GLP-1, or the analogue or agonist thereof, and may be selected from the group consisting of Exendin-4, Liraglutide, Taspoglutide, Albiglutide, Lixisenatide and Dulaglutide.

The term DPP4 inhibitor (DPP4i) refers to a class of oral hypoglycemics that block DPP-4 (DPP-IV). Glucagon increases blood glucose levels, and DPP-4 inhibitors reduce glucagon and blood glucose levels. The mechanism of DPP-4 inhibitors is to increase incretin levels (GLP-1 and GIP) which inhibit glucagon release, which in turn increases insulin secretion, decreases gastric emptying, and decreases blood glucose levels. DPP4i include compounds such as Sitagliptin, Vildagliptin, Saxagliptin, Linagliptin, Gemigliptin, Anagliptin, Teneligliptin, Alogliptin, Trelagliptin, Omarigliptin, Evogliptin, Gosogliptin and Dutogliptin.

The term "PAM" or "Positive Allosteric Modulator" refers to Positive allosteric modulators (PAMs) of GABAA and are well known to those of skill in the art. Illustrative PAMS include, but are not limited to alcohols {e.g., ethanol, isopropanol), avermectins {e.g., ivermectin), barbiturates {e.g., phenobarbital), benzodiazepines, bromides {e.g., potassium bromide, carbamates {e.g., meprobamate, carisoprodol), chloralose, chlormezanone, clomethiazole, dihydroergolines {e.g., ergoloid (dihydroergotoxine)), etazepine, etifoxine, imidazoles {e.g., etomidate), kavalactones (found in kava), loreclezole, neuroactive steroids {e.g., allopregnanolone, ganaxolone), nonbenzodiazepines (e.g., zaleplon, Zolpidem, zopiclone, eszopiclone), petri chloral, phenols (e.g., propofol), piped dinediones (e.g., glutethimide, methyprylon), propanidid, pyrazolopyridines (e.g., etazolate), quinazolinones (e.g., methaqualone), skullcap constituents (e.g. constituents of *Scutellaria* sp. including, but not limited to flavonoids such as baicalein), stiripentol, sulfonylalkanes (e.g., sulfonmethane, tetronal, trional), valerian constituents (e.g., valeric acid, valerenic acid), and certain volatiles/gases (e.g., chloral hydrate, chloroform, diethyl ether, sevoflurane) . The PAMs used in combination with the GABA receptor activating ligands may exclude alcohols, and/or kavalactones, and/or skullcap or skullcap constituents, and/or valerian or valerian constituents, and/or volatile gases. The PAM may comprise an agent selected from the group consisting of a barbituate, a benzodiazepine, a quinazolinone, and a neurosteroid. Illustrative barbituates include, but are not limited to allobarbital (5,5-diallylbarbiturate), amobarbital (5-ethyl-5-isopentyl-barbiturate), aprobarbital (5-allyl-5-isopropyl-barbiturate), alphenal (5-allyl-5-phenyl-barbiturate), barbital (5,5-diethylbarbiturate), brallobarbital (5-allyl-5-(2-bromo-allyl)-barbiturate), pentobarbital (5-ethyl-5-(1-methylbutyl)-barbiturate), phenobarbital (5-ethyl-5-phenylbarbiturate), secobarbital (5-[(2R)-pentan-2-yl]-5-prop-2-enyl-barbiturate), and the like. Illustrative benzodiazepines include, but are not limited to alprazolam, bromazepam, chlordiazepoxide, clonazepam, clorazepate, diazepam, estazolam, flurazepam, halazepam, ketazolam, lorazepam, nitrazepam, oxazepam, prazepam, quazepam, temazepam, triazolam, and the like. Illustrative neurosteroids include, but are not limited to allopregnanolone, and pregnanolone. Furthermore, the 2-cyano-3-cyclopropyl-3-hydroxy-n-aryl-thioacrylamide derivatives of the group 2-cyano-3-cyclopropyl-3-hydroxy-N-(3-methyl-4-trifluormethyl-phenyl)-thioacrylamide, 2-cyano-3-cyclopropyl-N-(4-fluoro-3-methyl-phenyl)-3-hydroxy-thioacrylamide, 2-cyano-3-cyclopropyl-3-hydroxy-N-(3-methyl-4-nitro-phenyl)-thioacrylamide, 2-cyano-N-(4-cyano-3-methyl-phenyl)-3-cyclopropyl-3-hydroxy-thioacrylamide, 2-cyano-3-cyclopropyl-3-hydroxy-N-(4-trifluoromethanesulfinyl-3-methyl-phenyl)-thioacrylamide, 2-cyano-3-cyclopropyl-3-hydroxy-N-(4-trifluoromethanesulfonyl-3-methyl-phenyl)-thioacrylamide, 2-cya no-3-cyclopropyl-3-hydroxy-N-(3-methyl-4-((trifluoromethyl)thio)phenyl)-thioacrylamide, and 2-cyano-3-cyclopropyl-N-(4-chloro-3-methyl-phenyl)-3-hydroxy-thioacrylamide, disclosed in WO2015140081 may be of use as PAMs in the present invention.

Within the present disclosure, the terms "intercellular" and "interstitial" are interchangeably used to describe small spaces located between cells.

DETAILED DESCRIPTION OF THE INVENTION

The present invention builds on new knowledge of the functional basis of gamma-aminobutyric acid (GABA) regulation of β cells in human pancreatic islets of Langerhans and the application of this knowledge in novel methods for treatment and prevention of disorders caused or influenced by dysfunction of β cells. The present invention also applies this knowledge to in vitro methods for screening for new therapeutic entities having therapeutic value in treatment and prevention of disorders caused or influenced by dysfunction of β cells.

A decreased first phase insulin response (FPIR) is considered an early indication of β-cell dysfunction. This phenomenon is seen in early in the disease progression in both type 1- and type 2-diabetes[41,42]. The extent of the FPIR is dependent on the pancreas's previous history of glucose stimulation. Upon repeated glucose stimulus during short intervals the FPIR is inhibited, however if longer intervals are used an increase in the FPIR is observed[43]. The high demand for insulin secretion places an enormous burden on the endoplasmic reticulum inside the β cells. This can in the in the long run lead to an aggregation of unfolded and misfolded proteins, a condition known as ER stress. This triggers the unfolded protein response (UPR) and protein translation is therefore temporarily halted. However if the UPR fails to alleviate the cell from ER stress and the ER function is compromised apoptosis of the β-cell is induced[44,45]. It has also been suggested that an inadequate or defective β-cell endoplasmic reticulum response results in the release of β-cell antigens and neoantigens that initiate autoimmunity[46]. It has also been suggested that an inadequate or defective β-cell endoplasmic reticulum response results in the release of β-cell antigens and neoantigens that initiate autoimmunity. Further, it has been shown that reduced insulin production relieves ER stress and induces β-cell proliferation (see "Reduced Insulin Production Relieves Endoplasmic Reticulum Stress and Induces β Cell Proliferation", Szabat, M., et al., Cell Metabolism, Volume 23, Issue 1, 12 Jan. 2016, Pages 179-193).

A decrease in insulin granule exocytosis in patients experiencing β-cell dysfunction could thus reduce the ER stress put on the β-cells, help preserve ER function to reduce induction of β-cell apoptosis and lower the amount of autoantigen released by β-cells, as well as stimulate the regeneration of β-cells. The experimental results shown in Example 4 suggest that GABA decreases the rate of insulin granule exocytosis in β cells.

It is known that GABA generally increases the amount of released insulin. As GABA decreases the rate of exocytosis, it follows that it also at the same time increases the amount of insulin released per insulin exocytosis event.

In a first aspect, the invention relates to a method for treatment or prevention of disorders caused or influenced by dysfunction of β cells by decreasing the rate of insulin granule exocytosis in a human patient, said method comprising administering to said patient a compound selected from the group consisting of $GABA_A$ receptor agonists.

In a further aspect, the invention relates to a method for treatment or prevention of disorders caused or influenced by dysfunction of 13 cells by increasing the amount of insulin released per insulin granule exocytosis event in a human patient, said method comprising administering to said patient a compound selected from the group consisting of $GABA_A$ receptor agonists.

In a further aspect, the invention relates to a method for treatment or prevention of disorders caused or influenced by dysfunction of β cells by decreasing the rate of insulin granule exocytosis while increasing the amount of insulin released per insulin granule exocytosis event in a human patient, said method comprising administering to said patient a compound selected from the group consisting of $GABA_A$ receptor agonists.

In a further aspect, the invention relates to a method for ameliorating symptoms of a disorder caused or influenced by dysfunction of 13 cells, wherein said ameliorating of symptoms comprises decreasing the rate of insulin granule exocytosis in a patient by administering to said patient a compound selected from the group consisting of $GABA_A$ receptor agonists.

In a further aspect, the invention relates to a method for decreasing the rate of insulin granule exocytosis in a patient comprising administering to said patient a compound selected from the group consisting of $GABA_A$ receptor agonists.

The methods according to the above aspects may be embodied as described below.

According to one embodiment, the insulin granule exocytosis may be first phase insulin secretion.

According to one embodiment, the insulin granule exocytosis may be second phase insulin secretion.

In one embodiment, the $GABA_A$ receptor agonist is administered in an amount effective to achieve an intercellular concentration of $GABA_A$ receptor agonist in the range of 100 to 1000 nM. The $GABA_A$ receptor receptor agonist does not normally penetrate the blood brain barrier.

According to one embodiment of the invention the $GABA_A$ receptor agonist is selected from the group consisting of GABA, muscimol, thiomuscimol, cis-aminocrotonic acid (CACA), homotaurine, bamaluzole, gabamide, GABOB, gaboxadol, ibotenic acid, isoguvacine, isonipecotic acid, phenibut, picamilon, progabide, quisqualamine, progabide acid (SL 75102).

According to one embodiment, the method of the invention further comprises administering glucagon-like peptide 1 (GLP-1), a dipeptidyl peptidase 4 inhibitor (DPP4i) or a Positive Allosteric Modulator of a $GABA_A$ receptor (PAM) wherein said PAM binds to the $\alpha 2$, $\alpha 5$ or $\beta 3$ $GABA_A$ receptor subunit and preferably does not bind to the al $GABA_A$ receptor subunit, to said human patient.

When GLP-1, or an analogue or agonist thereof, is administered in combination with GABA, they are to administered in relative concentrations. The concentration ratio GABA:GLP-1 is between 10 000:1 to 10:1, preferably 5000:1 to 100:1, and most preferably 500:1 to 200:1.

It has been shown that even after GLP-1 is eliminated from the circulation, the β-cells will remember the GLP-1 activation for up to 30 minutes after GLP-1 is no longer in circulation. During this time, the GABA signalling will continue to be elevated, even in the absence of GLP-1. Hence, the low levels of GLP-1 will suffice to improve the effect of the treatment.

DPP4i may be chosen from the group comprising Sitagliptin, Vildagliptin, Saxagliptin, Linagliptin, Gemigliptin, Anagliptin, Teneligliptin, Alogliptin, Trelagliptin, Omarigliptin, Evogliptin, Gosogliptin and Dutogliptin.

PAM may comprise a barbiturate, chosen from the group comprising of allobarbital (5,5-diallylbarbiturate), amobarbital (5-ethyl-5-isopentyl-barbiturate), aprobarbital (5-allyl-5-isopropyl-barbiturate), alphenal (5-allyl-5-phenyl-barbiturate), barbital (5,5-diethylbarbiturate), brallobarbital (5-allyl-5-(2-bromo-allyl)-barbiturate), pentobarbital (5-ethyl-5-(1-methylbutyl)-barbiturate), phenobarbital (5-ethyl-5-phenylbarbiturate), secobarbital (5-[(2R)-pentan-2-yl]-5-prop-2-enyl-barbiturate).

PAM may comprise a benzodiazepine, chosen from the group comprising of alprazolam, bromazepam, chlordiazepoxide, midazolam, clonazepam, clorazepate, diazepam, estazolam, flurazepam, halazepam, ketazolam, lorazepam, nitrazepam, oxazepam, prazepam, quazepam, temazepam, and triazolam.

PAMs may influence the subunit profile of the GABA receptor by means of, at least in part, altered expression. In particular, benzodiazepines are preferred within the aspects of the present invention, for obtaining the effect of normalizing the $GABA_A$ receptor subunit profile.

It is further known that pharmacological treatment using GABA agonists or receptor modulators can alter the expression of GABAA receptor subunits after long-term use due to desensitization of the receptor or other coping mechanisms (see for instance "Regulation of $GABA_A$ Receptor Subunit Expression by Pharmacological Agents", Uusi-Oukaru, M., Korpi, E. R., Pharmacol Rev 62:97-135, 2010). Given the surprising finding that $GABA_A$ receptor subunits are differently expressed in beta cells from type 2 diabetes patients compared to healthy controls, pharmacological treatment with GABA agonists or modulators that alter the expression of receptor subunits could provide a novel therapeutic approach.

Thus, in one aspect, the invention relates to a method of treating Type 2 Diabetes in a human subject comprising administering a Positive Allosteric Modulator (PAM) of a GABA receptor for a period of time and in an amount effective to normalize the $GABA_A$ receptor subunit profile in said subject.

According to one embodiment, the GLP-1 or DPP4i is administered in an amount effective to achieve an intercellular concentration of GLP-1 that is less than or equal to 0.5% of the intercellular concentration of $GABA_A$ receptor agonist.

The timing of the administration in relation to the ingestion of the meal, may be important as it has been proven that the blood serum level of GABA reaches a maximum approximately 45 minutes after administration in connection with ingestion of food. The blood serum levels of GABA markedly decreases after approximately 90 minutes from the administration of GABA.

Thus, according to one embodiment, the $GABA_A$ receptor agonist is administered to the human patient 60-180 minutes before ingestion of food, 60-120 minutes before ingestion of food, or 30-60 minutes before ingestion of food. The above mentioned timing of administration in relation to ingestion of food will ensure a maximum effect of the GABA and consequently the blood insulin levels.

In one embodiment, the method according to the invention is used for treatment of presymptomatic Type 1 diabetes of stage 1, presymptomatic Type 1 diabetes of stage 2, pre-Type 2 Diabetes, impaired glucose tolerance, Type 2 Diabetes, Type 1 Diabetes, and obesity.

Presymptomatic diabetes is defined in for instance "Staging Presymptomatic Type 1 Diabetes: A Scientific Statement of JDRF, the Endocrine Society, and the American Diabetes Association", Insel, R. I, et al., Diabetes Care 2015; 38:1964-1974.

In one embodiment, the method according to the invention is used for maintaining islet cells and islet cell function, such as beta cells and beta cell function.

In one embodiment, the method according to the invention is used for promoting islet cell growth and/or proliferation.

In one embodiment, the method according to the invention is used for preventing beta cell apoptosis.

In one embodiment, the method according to the invention is used for treatment or prevention of hyperinsulinaemia.

In a further aspect, the invention relates to the use of gamma-amino butyric acid (GABA), or a GABA receptor agonist, for use in a method for treatment, prevention, or ameliorating of symptoms according to the above.

In a further aspect, the invention relates to the use of gamma-amino butyric acid (GABA), or a GABA receptor agonist, in the manufacture of a pharmaceutical composition for use in a method according to the above.

Furthermore, it is disclosed herein that in Type 2 Diabetes, the GABA signalling in the β cells was altered and the subunit composition of the $GABA_A$ receptors was altered. Thus, in one aspect, the invention relates to methods for treatment of T2D comprising administering an effective amount of a compound that alters and normalized the subunit composition of the $GABA_A$ receptors.

In intact human islets, from nondiabetic and diabetic donors, we studied GABA regulation of its main target, the $GABA_A$ receptors that are ion channels opened by GABA. Importantly, in the human islets, insulin, glucagon and somatostatin secreting β, α and δ cells, respectively, all express the $GABA_A$ receptors[6]. This renders the human islet GABA signalling distinct from e.g. signalling in rodent islets where the $GABA_A$ receptors are only expressed by the α cells[15,16]. The results presented herein reveal that in human islets, GABA regulation of islet-specific $GABA_A$ receptors in β cells is multimodal, involves two subtypes of $GABA_A$ receptors and shapes hormone secretion. In diabetes, the GABA signalling in islets is altered.

The present inventors have also characterized β cell-specific high-affinity $GABA_A$ receptors and defined their pharmacological profile and further identified their modulation of exocytosis.

Given the critical functions attributed to GABA in the islets, like promoting β cells proliferation, α to β cells transformation, maintenance of β cell mass, survival of β cells and modulation of hormone secretion[1-6], a need to identify the targets of GABA in human islets was identified. Here we have identified and characterized in human pancreatic islets of Langerhans GABA-activated $GABA_A$ receptors subtypes in the β cells, for the purposes of the present disclosure termed "iGABA$_A$RI" and IGABA$_A$RII". These receptors are high-affinity, large conductance channels and can be selectively modulated by specific pharmaceuticals. When activated, these unique β cell-specific receptors decrease the rate of exocytosis in β cells and modulate glucose-stimulated insulin secretion.

The optimal GABA concentrations for active iGABA$_A$Rs ranged from 100 nM to submicromolar GABA, as shown in Example 3. However, at about 1 μM GABA the model revealed the channels were significantly starting to desensitize. The GABA$_A$ receptors are desensitized and stop working at concentrations exceeding 1000 nM. GLP-1 induced a long-term memory in the iGABA$_A$RI. This is in contrast to the CNS drugs where the enhancing effects ended when the drug was washed off the islets.

Our model exhibits GABA-primed closed and GABA-desensitized states like those seen in models for neuronal GAB$_A$AR-mediated currents (Jones and Westbrook, 1995; Lindquist et al., 2005) albeit with 100-fold higher affinity for GABA in the human islets. In T2D, the iGABA$_A$Rs, high conductance and very effective channels, become supersensitive to GABA. In the human β cells only two functional subtypes of GABA$_A$Rs were identified in contrast to the plethora of receptor types expressed in the brain. In islets from ND donors, the pentameric iGABA$_A$R consist of a combination of α2, α5, β3, γ2 subunits. Clearly a number of combinations are possible but the pharmacological profile of the receptors is consistent with α2β3γ2, α5β3γ2 and α2α5β3γ2 (Olsen and Sieghart, 2009). The receptors interact with the intracellular milieu that can further shape their characteristics as was apparent by the long-lasting effects of the GLP-1. In islets from individuals with T2D, potential subtypes include the α2β3γ2 but also α3β3γ2 and α2a3β3γ2 iGABA$_A$R receptors. GABA-activated Cl$^-$ currents have not been recorded in β cells in rodent islets, so far (Jin et al., 2013; Rorsman et al., 1989; Soltani et al., 2011; Wendt et al., 2004). However, in mouse β cells, Ca$^{2+}$ transients are modulated by GABA$_A$R agonists (Soltani et al., 2011) and single-cell transcriptome analysis has detected GABA$_A$R subunit genes in mouse islet β cells (GEO: GSE77980, FIG. 5b). The most prominent genes were α4β3δ whereas no or very low level of the γ2 subunit was detected resulting in, potentially, high-affinity GABAARs but with different pharmacological profile from the human receptors e.g. being insensitive to benzodiazepines (Olsen and Sieghart, 2009). Single-cell sequencing further showed that human β cells express only one of the two obligatory GABA$_B$R subunits in contrasts to e.g. mice where both subunits are expressed (GEO: GSE77980, FIG. 5c), suggesting that in human β cells, GABA signaling is dominated by the GABA$_A$R.

The inventor shows that the opening frequency and peak amplitude are different in alpha cells and beta cells giving bases to differentiate GABA analogues specific for the beta cells or alpha cells, giving the possibility to separately increase or decrease insulin production from the beta cells or separately increase or decrease the production of glucagon from the alpha cells. The inventor also found that the conductance in iGABA$_A$R-I is significantly higher in diabetes type 2 patients than in control individuals (see FIG. 1g).

Thus, in one aspect, the invention relates to a method for assessing therapeutic potential of a candidate compound, comprising measuring, in the presence of an iGABA$_A$R-agonist, the current through an iGABA$_A$R-molecule in the presence and absence, respectively, of said candidate compound wherein an increased or decreased current in the presence of the candidate compound indicates that candidate compound has a therapeutic potential.

In a further aspect, the invention relates to a method for assessing therapeutic potential of a candidate compound, comprising providing an islet cell from a diabetic donor and measuring the apparent affinity (Ka) for GABA of iGABA$_A$R-molecules in said cell in the presence and absence, respectively, of said candidate compound, wherein a higher apparent affinity in the presence of the candidate compound indicates that candidate compound has a therapeutic potential.

The results disclosed herein also provide a rationale for developments with focus on β cell-specific GABA$_A$R drugs, as common CNS drugs like diazepam, propofol, pentobarbital but not zolpidem, modulate the receptors. In accordance with the decreased total GABA content in islets from T2D donors, the induction of the very high-affinity iGABA$_A$R in T2D is likely to be a consequence of the disease and a compensatory response to maintain normal islet functions.

It is known that long-term use of ethanol or CNS drugs acting on GABA receptors alter the subunit composition of GABA receptors.

Thus, in a further aspect, the invention relates to a method of treating Type 2 Diabetes in a human subject comprising administering a Positive Allosteric Modulator (PAM) of a GABA receptor for a period of time and in an amount effective to normalize the GABA$_A$ receptor subunit profile in said subject.

In a further aspect, the invention relates to a method for assessing therapeutic potential of a candidate compound, comprising administering the candidate compound to a subject having at least one iGABA$_A$R supersensitive to GABA, for a period of time, and assessing whether the sensitivity to GABA has been decreased following said administration, e.g. to levels seen in non-diabetic donors. The sensitivity to GABA can be assessed and measured as described in the Examples. Said subject may be a human or an animal, such as a rodent (e.g. mouse or rat), monkey, dog, or pig.

In a further aspect, the invention relates to a method for assessing therapeutic potential of a candidate compound, comprising providing an islet cell from a diabetic donor and measuring the opening frequency of iGABA$_A$R-molecules in said cell in the presence and absence, respectively, of said candidate compound, wherein an increased opening frequency in the presence of the candidate compound indicates that candidate compound has a therapeutic potential.

According to one embodiment of the invention, the iGABA$_A$R- is iGABA$_A$RI.

According to one embodiment of the invention, the iGABA$_A$R is iGABAARII.

According to one embodiment of the invention, the therapeutic potential is in presymptomatic Type 1 diabetes of stage 1, presymptomatic Type 1 diabetes of stage 2, pre-Type 2 Diabetes, impaired glucose tolerance, Type 2 Diabetes, Type 1 Diabetes or obesity.

EXAMPLES

Example 1

GABA-Activated Currents in Intact Human Islets

Figure 6:
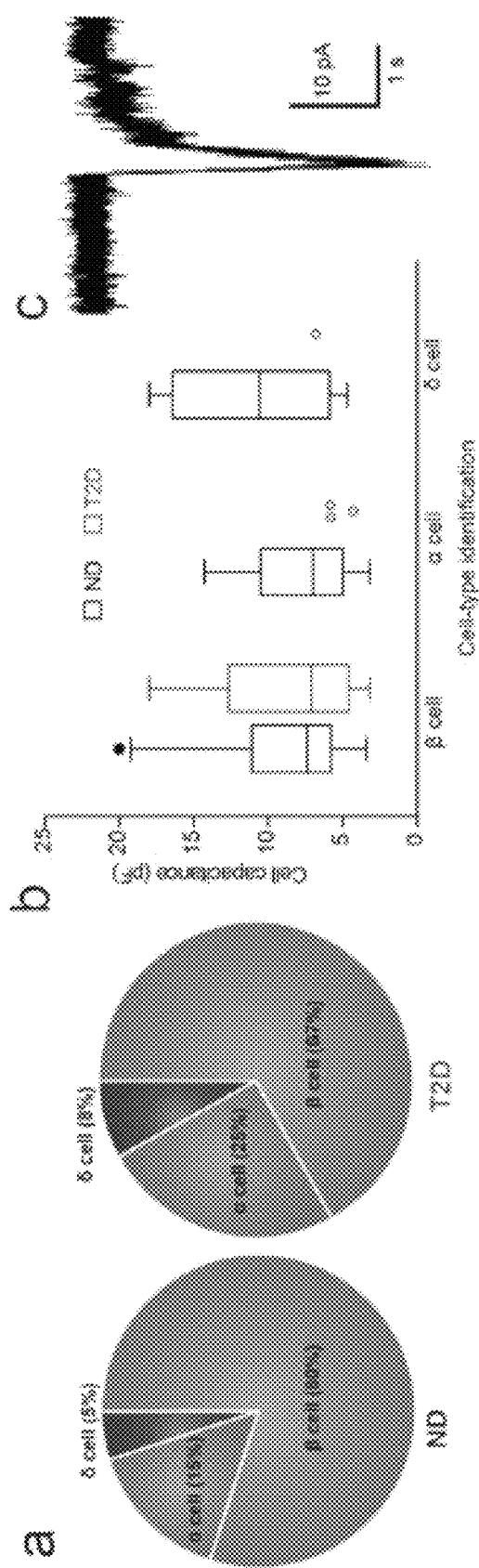
FIG. 6: Human islet cell-type identification, cell capacitance measurement and interstitial GABA-activated current in δ cells. (a) Pie charts showing the percentage of each islet cell-type (β, α, and δ cell) determined by single cell RT-PCR from ND (n=38) and T2D (n=6) donors. The total number of identified single-hormone expressing cells is 93. (b) The whole-cell capacitance of each islet cell-type (β, α and δ cell) from ND and T2D donors. Data are presented as box and whiskers plot with median and whiskers plotted by Tukey method to determine outliers (, above the whiskers). The statistical analysis was performed without outliers. There was no significant difference in the cell capacitance among different cell-types (P>0.05, Kruskal-Wallis ANOVA on ranks). Data from cell-type having less than 4 cells are presented as a scatter plot. (c) Representative synaptic-like current recorded from a δ cell in an intact human islet in the absence of exogenously added GABA. The extracellular solution contained 20 mM glucose. Recording was done in the whole-cell voltage-clamp configuration at the holding potential Vp=−70 mV at room temperature.

We used whole-cell patch-clamp (Hamill et al., 1981) to study single GABAA receptor channels in intact islets from nondiabetic (ND) and clinically diagnosed T2D donors. The GABAA receptor is a transmembrane, pentameric plasma membrane protein complex that contains an integral Cl$^-$ ion channel. The channel is normally closed but it opens when GABA binds to the GABAA receptor. The current through a single GABAA receptor is the single-channel current and is manifested in the recording by a deflection (step-opening) from baseline where the channels are closed (Eghbali et al., 1997). Cells were blindly selected for recording (FIG. 1a; Jin et al., 2011) and the cell-type was determined post-hoc by single-cell RT-PCR analysis of the islet hormone transcripts; glucagon (for a cells), insulin (β cells) and somatostatin (δ cells). GABA-activated currents were recorded from 383 cells in islets from 109 donors (FIG. 1a, b), and 93 cells expressing single hormone transcript could be determined from 38 ND and 6 T2D donors (FIG. 1c, FIG. 6a). The majority of identified cells are β cells (FIG. 6a). Cell capacitance measurement revealed no difference in the median size between different cell-types or between cells from ND and T2D islets (FIG. 6b). While the cell-type could not be defined from the size of the cell, the interstitial GABA-activated current characteristics were cell-type specific (FIG. 1b). The GABAA receptor single-channel currents had low open probability in the a cells in stark contrast to the β cells were the channel openings were prominent. In d cells, transient, synaptic-like currents were recorded (FIG. 6c).

Example 2

GABA-Activated Receptors in β Cells

We further analyzed the GABA-activated single-channel currents in the β cells. $GABA_A$ receptors ($GABA_A$Rs) can be characterized based on conductance, current kinetics and the receptor's pharmacology. We identified two types of $GABA_A$Rs and termed them islet-$GABA_A$ receptor I and II, $iGABA_A$RI and $iGABA_A$RII respectively, based on the single-channel current distributions (FIG. 1d). The currents were inhibited by picrotoxin, a specific $GABA_A$R antagonist. Representative traces of the currents recorded from ND or T2D islet β cells activated by sequentially applied GABA concentrations are shown in FIG. 1e. When activated by interstitial GABA, the single-channel current varied linearly with the membrane potential and the cord conductance for the $iGABA_A$RI and RII channels were 37 pS and 76 pS (FIG. 1f), respectively.

GABA is released from β β and d cells (Braun et al., 2010) and the interstitial concentration will vary with the physiological activity of the islet. In plasma from ND and T2D donors the GABA concentration was similar, 516+30 nM (n=10) and 480+28 nM (n=13), respectively. Currently it is not known what the effective GABA concentration is in the islets. We, therefore, applied a range of GABA concentrations to islets, from 1 to $10^4$ nM, to open the channels and examined the effects of GABA on the channel activation, conductance and kinetics (FIG. 1, 2). In >10 nM GABA, GABA-activated Cl$^-$ currents were evoked. The average conductance of single $iGABA_A$R channel was generally not dependent on the GABA concentration (FIG. 1g) but, interestingly, the 100 nM GABA-activated iGABAARI conductance (55±5 pS) recorded in islets from T2D donors was significantly larger than the conductance recorded in islets from ND donors (41±3 pS, P<0.05). All GABA-activated currents were inhibited by the GABAAR antagonists picrotoxin (100 μM) or SR95531 (100 μM). We also examined effects of temperature on the channels as GABAARs commonly have a number of subconductance states (Gage and Chung, 1994; Verdoorn et al., 1990). The average conductance of single iGABAARI channels was temperature dependent and increased by a factor of 1.3 in interstitial, 10 and 100 nM GABA as the temperature was raised from RT (20-22° C.) to 34° C. (FIG. 1g).

The membrane potential of β cells can vary over a wide range (Braun et al., 2010; Rorsman and Braun, 2013). We examined how the open probability (Po) of the $iGABA_A$R channels varied with membrane potential displacement away from the chloride reversal potential (ECl$^-$). We have previously shown for $GABA_A$R channels that it is the displacement from the chloride reversal, and not the exact potential value, that determines the conductance characteristics (Birnir et al., 1994). The Po of the channels is related to both the frequency of openings and the mean open time (To) for the channels. The average Po of the GABA-activated iGABAARs was potential dependent and increased with positive membrane potential displacements (FIG. 1h). The mean current (Imean) is related to both the conductance and the Po of the channels. It is the ensemble of GABA-activated currents in the cell. The Imean was outwardly rectifying (FIG. 1i) revealing that the $iGABA_A$R effect on the membrane potential increases as the membrane potential is depolarized past the ECl$^-$. At these potentials, opening of $iGABA_A$R channels promotes repolarization of the membrane potential whereas at potentials more negative than ECl$^-$, activation of $iGABA_A$R channels contributes to the excitation of the 0 cells. We further examined if the Imean and the Po of the channels were regulated by either GABA concentration or T2D (pipette potential Vp=-70 mV). Interestingly, both 100 nM GABA and T2D significantly (P<0.05) enhanced Po (FIG. 1j) and Imean (FIG. 1k) of the $iGABA_A$R channels.

Example 3

In Diabetes $iGABA_A$Rs are Supersensitive to GABA

As the effects on Po and $I_{mean}$ can only be partially explained by modulation of channel conductance we examined further the kinetic properties of the channels. GABA increased the rate (frequency) of $iGABA_A$R channel openings in islets from both ND and T2D donors but did not affect the mean open times To. Importantly, the frequency of openings was significantly increased in islets from T2D donors resulting in higher apparent affinity for GABA (FIG. 2). At saturating GABA concentrations, the channels desensitized i.e. stopped working (FIG. 2). The data could be fitted with a model (FIG. 2a) comprised of 3 closed states: a GABA-free (C), GABA-bound state primed for channel opening (C*) and a GABA-bound desensitized state (Cd). The model has two open states where of one (OS) represents spontaneous openings and the other (OG) occurs in the GABA-primed state. For $iGABA_A$RI, the maximal rate (frequency) of channel openings was in 100 nM GABA, but the opening rate decreased at micromolar concentrations (FIG. 2b, c). The apparent affinity for GABA (Ka) at room temperature (RT) was 20 nM for $iGABA_A$RI, which was significantly lower (P<0.05) than 65 nM for iGABAARII. Both channel types have similar equilibrium constants for desensitization (Kd), in the micromolar range. The To of iGABAARI was 3-fold lower (P<0.05) than for $iGABA_A$RII and this is reflected in the closing rates (kc). The opening rates of the $iGABA_A$Rs were similar in interstitial and 10 nM GABA suggesting that the interstitial GABA concentration under our experimental conditions is about 10 nM. Raising the temperature to 34° C. resulted in a 2-fold reduction in To for $iGABA_A$RI but no change in opening rate. However, for $iGABA_A$RII, raising the temperature to 34° C. had no effect on To but did increase Ka 23-fold and shifted the peak opening rate from 100 nM to 1 μM GABA (FIG. 2a, c).

Interestingly, this shift in GABA activation was associated with the appearance of a non-zero baseline in the opening rate in the [GABA] range 10-100 nM, indicating the presence of spontaneous channel openings. In islets from T2D donors, the data were described by the same model and had similar To and Kd as those from ND donors (FIG. 2d, e). However, the Ka for GABA activation of the iGABA$_A$Rs was reduced at RT by 6-fold for iGABA$_A$RI and at 34° C. by ~3-fold for iGABA$_A$RI and 300-fold for iGABA$_A$RII. In addition, the opening rate of the iGABA$_A$RI was significantly higher than recorded in islets from ND donors. Together the results show that in T2D the functional response of the iGABAARI and II in pancreatic islets is altered. Furthermore, the total GABA content in ND and T2D islets was significantly different (P<0.05) being 7.7±2.2 nmol/mg protein (n=7) and 1.6±0.5 nmol/mg protein (n=6), respectively.

We investigated further at the single cell transcriptome level if changes in expression of iGABA$_A$R subunits had occurred. Data from single cell RNA sequencing (GEO: GSE81608 and ArrayExpress: E-MTAB-5060) shown in FIG. 2f revealed that the profile of the expressed GABAA subunits is altered in β cells from T2D (n=395 cells) as compared to ND (n=376 cells) donors. The classical GABAB receptor is not expressed in the β cells as only one, GABABR1, of the required two subunits of the dimeric GABAB receptor (Xu et al., 2014) was expressed in the cells (FIG. 5a).

Example 4

GABA Shapes Insulin Exocytosis and Secretion

We examined the effect of GABA on insulin granule exocytosis using the total internal reflection fluorescence (TIRF) microscopy on cells expressing the fluorescent granule-marker neuropeptide-Y (NPY)-Venus. Depolarization of the cells by local application of 75 mM K$^+$ caused a fraction of the granules to undergo exocytosis, detected as sudden disappearance of fluorescence when NPY-Venus was released (FIGS. 3a-3c). Exocytosis corresponding to ~210 granules/min for an average-sized cells was observed in control (3.5±0.4·10$^{-3}$·tm$^{-2}$·s$^{-1}$, n=6), which decreased to ~150 granules/min in presence of 100 nM GABA (2.5±0.6·10$^{-3}$·tm$^{-2}$·s$^{-1}$, p<0.05, n=7, FIGS. 3c-3e). The loss of NPY-Venus from individual granules was somewhat faster in presence of GABA compared with control (0.86±0.09 vs 1.28±0.13s, P<0.024, Wilcoxon Signed Rank test; n=119 and 96 granules; FIGS. 3c, 3f, and 3g). Release was usually preceded by a transient fluorescence increase (84±3% in control, n=119, FIG. 3f), which marks the opening of a fusion pore that is too narrow to allow peptide release (Obermuller et al., 2005; Tsuboi and Rutter, 2003). No changes were detected in the rising phase of the fluorescence signal, which reflects the fusion pore life-time (FIG. 3f).

Figure 7:
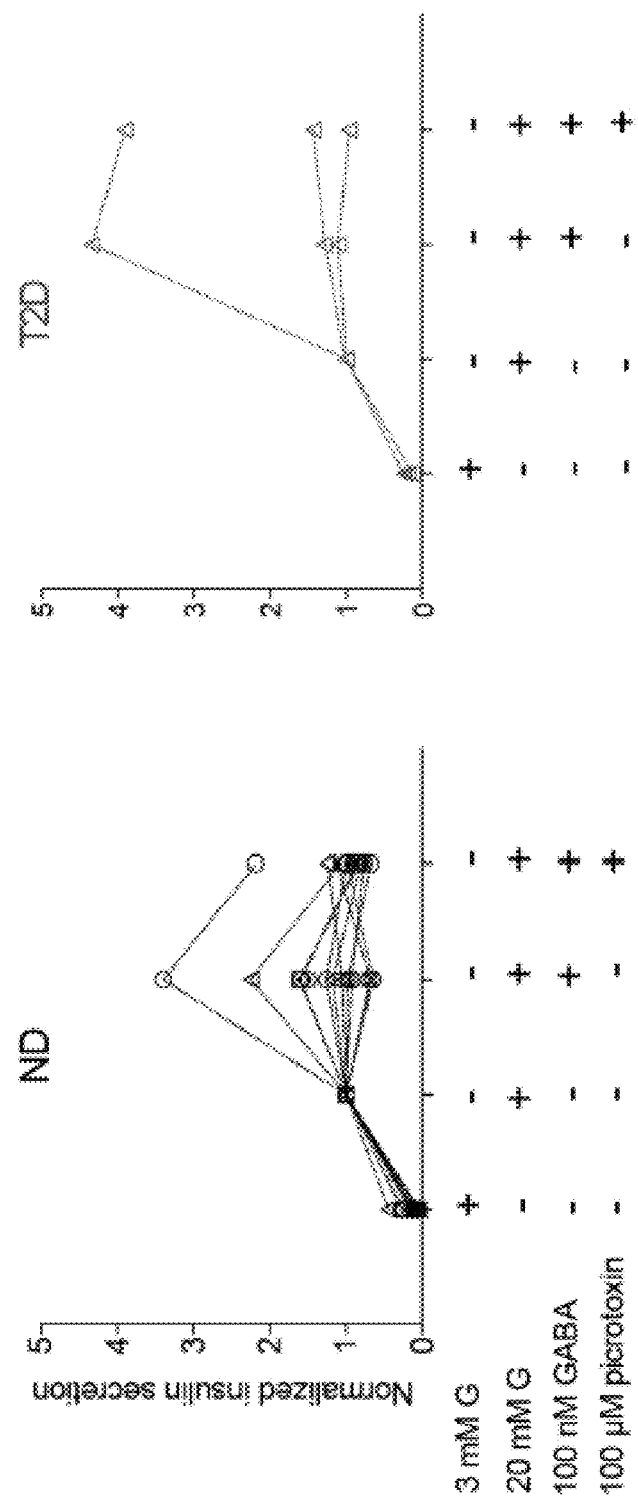
FIG. 7: Effect of GABA on glucose-stimulated insulin secretion in human islets. Insulin secretion was measured from human islets where test compounds were either incubated (30 min) with the islets (open circles) or applied sequentially (5 min) to islets (open triangles). Data were calculated as percentage of insulin content and further normalized to the level of 20 mM glucose response. On average, 100 nM GABA increased insulin secretion in 10 ND donors approximately 60% (1.6±0.2, n=10, P<0.05), which was reversed by picrotoxin. However, in islets from three ND donors GABA consistently decreased insulin secretion (0.7±0.01, P<0.05), but even these effects were reversed by picrotoxin. GABA increased insulin secretion in islets from one T2D donor, while it was without effect in two others. G, glucose. ND donors, n=13; T2D donors, n=3. Dotted lines identify results from islets from the same donor.

We also recorded exocytosis in cells bathed in 20 mM glucose for >10 min, as during 2$^{nd}$ phase insulin secretion. In cells from two ND donors, exocytosis was 0.11±0.02·10$^{-3}$·tm$^{-2}$·s$^{-1}$ (n=7), corresponding to ~7 granules per minute. With GABA present, exocytosis decreased slightly to 0.095±0.01·10$^{-3}$·tm$^{-2}$·s$^{-1}$ (~5 granules/min, P<0.05, n=6). A similar effect was seen in islet cells from one T2D donor with 0.031±0.010·10$^{-3}$·tm$^{-2}$·s$^{-1}$ (~2 granules/min) in control compared with 0.019±0.008·10$^{-3}$·tm$^{-2}$·s$^{-1}$ (~1 granules/min) with GABA (p<0.05, FIG. 3h, i). Taken together these data suggest that GABA decreases the rate of exocytosis in β cells. In glucose-stimulated islets, the modulatory effect of GABA on insulin secretion was more complex (FIG. 7) and is in line with the influence of paracrine factors (Caicedo, 2013) and differences in electrophysiological behavior of isolated versus islet β-cells (Rorsman and Ashcroft, 2018).

Example 5 iGABAARs are Selectively Modulated by Drugs

Many central nervous system (CNS) drugs commonly used clinically are thought to target only neuronal GABAARs (Hanson et al., 2008; Olsen and Sieghart, 2009; Sieghart, 2015). We examined if a benzodiazepine (diazepam), anesthetics (propofol, pentobarbital) and a hypnotic (zolpidem) also modulated the iGABAARs (FIG. 4a). Diazepam and zolpidem bind to receptors containing the g2 GABAAR subunit while zolpidem is, additionally, highly selective for receptors containing the al GABAAR subunit. Propofol and pentobarbital potentiate most CNS GABAAR subtypes. In the human islets, importantly, only zolpidem (100 or 200 nM) did not modulate the iGABAAR currents (FIG. 4a). The results are in agreement with the GABAAR subunit expression profile of the β cells (see FIG. 2f).

We further examined if GLP-1, a peptide secreted by L-cells in the gut and enhances insulin secretion, modulated the iGABAARs. GLP-1 (50 pM) increased the frequency of the iGABAARI channel openings (FIG. 4b). Remarkably, the current enhancement by GLP-1 remained, albeit at a reduced level, when the GLP-1 application was terminated (FIG. 4b). This long-lasting current enhancement was also recorded for iGABAARs in an islet from T2D individual.

Methods.

Intact Human Pancreatic Islets

Human islets were generously provided by the Nordic Network for Clinical Islet Transplantation, supported by EXODIAB and the Juvenile Diabetes Research Foundation. All procedures were approved by the regional ethics committee in Uppsala and informed consent obtained by appropriate measures from donors or their relatives. Islets were obtained from ND and T2D (HbA1c=6.5±0.16, mean±standard error of the mean, SEM) donors and isolated using collagenase digestion and Biocoll gradient centrifugation (Fred et al., 2010), separately for each pancreas. The islets were then hand-picked and cultured free-floating in CMRL 1066 (ICN Biomedicals, Costa Mesa, CA, USA) supplemented with 10 mM HEPES, 2 mM L-glutamine, 50 jig/ml gentamicin, 0.25 jig/ml fungizone (GIBCO, BRL, Gaithersburg, MD, USA), 20 jig/ml ciprofloxacin (Bayer Healthcare, Leverkusen, Germany), and 10 mM nicotinamide at 37° C. in humidified atmosphere containing 5% CO2, vol/vol and used in the experiments from second day of incubation up to 10 days of culturing.

Electrophysiological Experiments

The whole-cell patch-clamp configuration was obtained on intact islets using the blind patch-clamp technique (Hamill et al., 1981; Jin et al., 2011; Neher and Sakmann, 1976) and single-channel currents were recorded at room temperature (20-22° C.) or at 34° C. The single intact islet was held by the holding pipette and approached by the recording pipette from the other side (see FIG. 1a). The holding and recording pipettes were made from borosilicate glass. During experiments, the pancreatic islets were perfused with the extracellular solution (mM): 137 NaCl, 5.6 KCl, 2.6 CaCl2, 1.2 MgCl2, 10 HEPES and 20 glucose (pH 7.4 using NaOH) at the rate of 3 mL/min. The intracellular solution consisted of (mM): 135 CsCl, 30 CsOH, 1 MgCl2, 10 EGTA, 5

HEPES and 3 Mg-ATP (pH 7.2 with HCl). Drugs were purchased from Sigma-Aldrich (Steinheim, Germany) or Ascent Scientific (Bristol, UK). Pentobarbital, propofol, GLP-1 and the GABAAR antagonist SR95531 were dissolved in the extracellular solution. Diazepam, zolpidem and the GABAAR antagonist picrotoxin stock solutions were made in dimethyl sulfoxide (DMSO) and then dissolved in the extracellular solution. The final concentration of DMSO was 0.1% and did not affect the recordings (Eghbali et al., 1997). Recordings were done using an Axopatch 200B amplifier, filtered at 2 kHz, digitized on-line at 10 kHz using an analog-to-digital converter and Clampex 10.5 (Molecular Devices, CA, USA) software. The access resistance was monitored and if it changed by more than 25%, the recording was rejected. The single-channel parameters (amplitude, frequency/opening rate, conductance, open probability Po, mean current Imean and mean open time To) were analyzed by Channel3 (Nicholas Laver, Derek Laver, the University of Newcastle, Australia) and Clampfit 10.5 (Molecular Devices, USA). We used a simplified version of a model, previously established by Jones and Westbrook (Jones and Westbrook, 1995) to describe the activation of GABAA receptors (see FIG. 2a model scheme). Simulations of opening rate and mean open time were generated from this theoretical model using the 'Q-matrix' method of Colquhoun and Hawkes (Colquhoun and Hawkes, 1981, 1982). We accounted for the effects of missed events due to filtering using the 'effective rate constant' method of Blatz and Magleby (Blatz and Magleby, 1986) incorporating an event dead-time of 0.1 ms.

Cytoplasm Harvest and Single-Cell Reverse Transcription Polymerase Chain Reaction (RT-PCR)

The procedure for cytosome harvesting and single-cell RT-PCR have been previously described (Jin et al., 2013). In brief, the cytosome of the cell was harvested in the recording pipette by applying a negative pressure to the pipette at the end of patch-clamp recordings. The harvesting was terminated immediately before or as soon as the seal broke. The content in the pipette (around 5 µl) was expelled to a 0.2 ml RNase-free PCR tube that was immediately frozen on the dry ice and then stored at −80° C. The pipette solution and recoding pipettes were autoclaved and the recording electrode was cleaned with 70% ethanol followed by cleaning with RNAase away (Thermo Scientific). The harvested cytosome was subjected to the reverse transcription (RT) step that was performed with Verso™ cDNA synthesis kit (Thermo Scientific). The 20 µl reverse transcription reaction was incubated at 42° C. for 30 min followed by a second incubation at 95° C. for 2 min. PCR was performed in a 10 µl reaction mixture containing 3 µl cDNA, 5×SYBR Green I (Life Technologies), 1x PCR reaction buffer, MgCl2 (3 mM), dNTP (0.3 mM), 1×ROX reference dye, 0.8 U Jump-Start Taq DNA polymerase (Sigma-Adrich; Jin et al., 2011) and hormone gene-specific primers. The PCR amplification was performed using the ABI PRISM 7900 HT Sequence Detection System (Applied Biosystems) with an initial denaturation step of 5 min at 95° C., followed by 45 cycles of 95° C. for 15 s, 60° C. for 30 s and 72° C. for 1 min, and one melting curve step. The primers for hormone genes are insulin (1-forward: AGAGGCCATCAAGCAGAT-CACTGT (SEQ ID NO: 1), 1-reverse: CTGCGGGCTGCGTCTAGTTG (SEQ ID NO: 2); 2-forward: CCATCAAGCAGATCACTG (SEQ ID NO: 3), 2-reverse: CACTAGGTAGAGAGCTTCC (SEQ ID NO: 4)), glucagon (1-forward: AAGGCGAGAT-TTCCCAGAAGAGG (SEQ ID NO: 5), 1-reverse: ACGTGGCTAGCAGGTGATGTT (SEQ ID NO: 6); 2-forward: GCAACGTTCCCTTCAAGACAC (SEQ ID NO: 7), 2-reverse: ACTGGTGAATGTGCCCTGTG (SEQ ID NO: 8)), and somatostatin (1-forward: GCTTTAG-GAGCGAGGTTCGGA (SEQ ID NO: 9), 1-reverse: GGG-CATCATTCTCCGTCTGGT (SEQ ID NO: 10); 2-forward: CCCAGACTCCGTCAGTTTCT (SEQ ID NO: 11), 2-reverse: AAGTACTTGGCCAGTTCCTGC (SEQ ID NO: 12)). The PCR product was examined by the melting curve and/or run on a 1.5% agarose gel stained with SYBR Gold DNA gel stain (Life Technologies). Total RNA samples from human islets and the intracellular solution or water served as the positive control and negative control, respectively.

GABA$_A$R Subunits Expression Profile in Human and Mouse δ Cells from Single-Cell RNA-seq Data To examine the GABA receptor subunits expression in human and mouse β cells, two published datasets for islet single-cell RNA-seq from human ND and T2D donors (Segerstolpe et al., 2016; Xin et al., 2016b) and one dataset from mouse (GEO: GSE77980, (Xin et al., 2016a)) were downloaded. The RPKM values (reads per kilobase of transcript per million mapped reads) of GABA receptor subunits from annotated β cells were extracted and plotted.

Exocytosis Imaging

The islets were dissociated into single cells in 0.0025% trypsin in cell dissociation buffer (Hank's based) for 3-5 minutes. Cells were washed once in serum-containing medium, plated onto 22-mm polylysine-coated coverslips and allowed to settle overnight. Adenovirus particles adNPY-Venus (Tsuboi et al., 2006) or adNPY-mCherry (Meur et al., 2010) was added and cells were imaged 24-36 hours later. Cells selected for experiments expressed the granule marker and appeared healthy. Cells were imaged in a standard solution containing (mM): 138 NaCl, 5.6 KCl, 1.2 MgCl2, 2.6 CaCl2, 20 D-glucose, 5 HEPES (pH 7.4 with NaOH) (Barg et al., 2002; Gandasi and Barg, 2014). For depolarization dependent exocytosis experiments, glucose was 10 mM and the solution supplemented with 2 µM forskolin and 200 µM diazoxide, a K$^+$-ATP-channel opener that prevents glucose-dependent depolarization. Exocytosis was then evoked with high K$^+$ solution (75 mM KCl equimolarly replacing NaCl). High K$^+$ was applied by computer-timed local pressure ejection through a glass pipette similar to those used for patch clamp. All experiments were carried out at ~32° C. Cells were imaged using a custom-built lens-type total internal reflection (TIRF) microscope based on an Axiovert 135 microscope with a 100×/1.45 objective (Carl Zeiss). Excitation was from a DPSS laser at 491 (Cobolt, Stockholm, Sweden), controlled with an acousto-optical tunable filter (AA-Opto, France) and using dichroic Di01-R488/561 (Semrock) and emission filter FF01-523/610 (Semrock). Scaling was 160 nm per pixel and exposure time 100 ms per frame at 10 frames/s. Exocytosis events were found by eye. The moment of exocytosis was defined as the first significant change (2 standard deviations) from the pre-exocytosis baseline. This definition applied to both types of events, with or without preceding flash. The decay time was then defined as the time from exocytosis until the signal reached less than one third of the amplitude of the event. Traces were read out as DF, defined as average fluorescence in a 0.5 µm circle minus the average fluorescence in a surrounding annulus of 0.8 µm. The point of exocytosis was calculated by fitting the granule fluorescence during exocytosis with a discontinuous function (Eq 1), which assumes constant fluorescence before fusion, an inverted exponential decay just after fusion, and finally exponential decay during content release:

$$c = A1 \text{ for } t < t1 \qquad \text{Eq 1}$$
$$c = A2 + (A1 - A2)e^{-\frac{t-t1}{\tau 1}} \text{ for } t2 > t \geq t1$$
$$c = A3 + \left((A2 + (A1 - A2)e^{-\frac{t2}{\tau 1}}) - A3\right)e^{-\frac{t-t2}{\tau 2}} \text{ for } t \geq t2,$$

where t is time; c is average fluorescence in a 0.48 μm wide circle at the granule site; A1, A2 and A3 are the fluorescence values at the plateaus; τ1 and τ2 are the decay constants for the fluorescence increase after fusion and content release; and t1 and t2 are the times of fusion and release, respectively.

GABA Concentration Measurement in Human Islets with GABA ELISA

The individual islets were collected (between 20 and 900 islets from each donor) and after adding 450 μL water into Eppendorf tube containing islets, homogenized by two sessions of 10-second sonication with 1 min break between sonications, keeping the samples on ice during the break. After 2-minute centrifugation of the homogenate at 14 000 rpm, 350 μL of the supernatant were collected for subsequent GABA concentration measurement with GABA ELISA (BA E-2500, LDN, Germany), and 50 μL of the same supernatant were taken for protein measurement by improved Lowry assay with the Bio-Rad DC™ Protein Assay (USA). Obtained actual GABA concentration was normalized to protein concentration and expressed in nmol/mg protein for each sample.

Measurements of Insulin Secretion

Groups of 10-15 size-matched islets were preincubated for 30 min at 37° C. in experimental buffer containing 3 mM glucose followed by 40 min incubation in 500 μL buffer containing 3 or 20 mM glucose with or without GABA and picrotoxin. The incubation medium was subsequently collected, the islets sonicated briefly (1-2 periods of 10 s) in acidic ethanol and frozen overnight. Samples from the medium and the islets were appropriately diluted and analyzed in duplicates for insulin using an immunoassay kit from Mesoscale Discovery (Rockville, MD, USA). Secretion was normalized to insulin content and expressed in relation to that at 20 mM glucose. In some experiments, the islets were placed in a closed 10-μL Teflon tubing perfusion. The chamber was perfused with buffer at a rate of 60 μL/min (AutoMate Scientific, Berkeley, CA). After 30 min of equilibration in buffer with 3 mM glucose, the perfusate was collected in 5-min fractions (Biocollector, Atto Corp, Tokyo, Japan) while changing the glucose concentration, or adding GABA or picrotoxin. Three fractions were collected for each condition and analyzed for insulin. The results are presented as one data point per condition, which represents the average of the last two fractions at that condition. The first fraction was excluded since it was influenced by the preceding condition.

Statistical Analysis

Statistical analysis was performed using the two-tailed unpaired Student's t-test and Mann-Whitney test (for two groups comparison), one-way ANOVA and Kruskal-Wallis ANOVA on ranks (for multiple comparisons) using GraphPad Prism 7 software (GraphPad Software, USA). The Tukey method was used to detect the outliers. P values<0.05 were considered statistically significant. All data are presented as mean±SEM and plotted with GraphPad Prism 7.

All references cited herein are expressly incorporated in their entirety by reference.

REFERENCES

1 Soltani, N. et al. GABA exerts protective and regenerative effects on islet beta cells and reverses diabetes. *Proc Natl Acad Sci USA,* doi:1102715108 [pii] 10.1073/pnas.1102715108 (2011).

2 Tian, J. et al. gamma-Aminobutyric acid regulates both the survival and replication of human beta-cells. *Diabetes* 62, 3760-3765, doi:db13-0931 [pii] 10.2337/db13-0931 (2013).

3 Ben-Othman, N. et al. Long-Term GABA Administration Induces Alpha Cell-Mediated Beta-like Cell Neogenesis. *Cell* 168, 73-85 e11, doi:S0092-8674(16)31523-9 [pii] 10.1016/j.cell.2016.11.002 (2017).

4 Li, J. et al. Artemisinins Target GABAA Receptor Signaling and Impair alpha Cell Identity. *Cell* 168, 86-100 e115, doi:S0092-8674(16)31531-8 [pii] 10.1016/j.cell.2016.11.010 (2017).

5 Lawlor, N. et al. Single-cell transcriptomes identify human islet cell signatures and reveal cell-type-specific expression changes in type 2 diabetes. *Genome Res* 27, 208-222, doi:gr.212720.116 [pii] 10.1101/gr.212720.116 (2017).

6 Braun, M. et al. Gamma-aminobutyric acid (GABA) is an autocrine excitatory transmitter in human pancreatic beta-cells. *Diabetes* 59, 1694-1701, doi:db09-0797 [pii] 10.2337/db09-0797 (2010).

7 Taneera, J. et al. gamma-Aminobutyric acid (GABA) signalling in human pancreatic islets is altered in type 2 diabetes. *Diabetologia* 55, 1985-1994, doi:10.1007/s00125-012-2548-7 (2012).

8 Li, J. et al. Study of GABA in Healthy Volunteers: Pharmacokinetics and Pharmacodynamics. *Front Pharmacol* 6, 260, doi:10.3389/fphar.2015.00260 (2015).

9 Tian, J. et al. Gamma-aminobutyric acid inhibits T cell autoimmunity and the development of inflammatory responses in a mouse type 1 diabetes model. *J Immunol* 173, 5298-5304, doi:173/8/5298 [pii] (2004).

10 Bjurstom, H. et al. GABA, a natural immunomodulator of T lymphocytes. *J Neuroimmunol* 205, 44-50, doi:S0165-5728(08)00389-5 [pii] 10.1016/j.jneuroim.2008.08.017 (2008).

11 American, A. D. 2. Classification and Diagnosis of Diabetes. *Diabetes Care* 40, S11-S24, doi:40/Supplement-1/S11 [pii] 10.2337/dc17-S005 (2017).

12 Caicedo, A. Paracrine and autocrine interactions in the human islet: more than meets the eye. *Semin Cell Dev Biol* 24, 11-21, doi:S1084-9521(12)00172-3 [pii] 10.1016/j.semcdb.2012.09.007 (2013).

13 Rodriguez-Diaz, R. & Caicedo, A. Neural control of the endocrine pancreas. *Best Pract Res Clin Endocrinol Metab* 28, 745-756, doi:S1521-690X(14)00072-4 [pii] 10.1016/j.beem.2014.05.002 (2014).

14 Rorsman, P. & Braun, M. Regulation of insulin secretion in human pancreatic islets. *Annu Rev Physiol* 75, 155-179, doi:10.1146/annurev-physiol-030212-183754 (2013).

15 Rorsman, P. et al. Glucose-inhibition of glucagon secretion involves activation of GABAA-receptor chloride channels. *Nature* 341, 233-236, doi:10.1038/341233a0 (1989).

16 Jin, Y., Korol, S. V., Jin, Z., Barg, S. & Birnir, B. In intact islets interstitial GABA activates GABA(A) receptors that generate tonic currents in alpha-cells. *PLoS One* 8, e67228, doi:10.1371/journal.pone.0067228 PONE-D-13-10264 [pii] (2013).

17 Hamill, O. P., Marty, A., Neher, E., Sakmann, B. & Sigworth, F. J. Improved patch-clamp techniques for high-resolution current recording from cells and cell-free membrane patches. *Pflugers Arch* 391, 85-100 (1981).

18 Jin, Z., Jin, Y. & Birnir, B. GABA-activated single-channel and tonic currents in rat brain slices. *J Vis Exp*, doi:2858 [pii] 10.3791/2858 (2011).

19 Verdoorn, T. A., Draguhn, A., Ymer, S., Seeburg, P. H. & Sakmann, B. Functional properties of recombinant rat GABAA receptors depend upon subunit composition. *Neuron* 4, 919-928, doi:0896-6273(90)90145-6 [pii] (1990).

20 Gage, P. W. & Chung, S. H. Influence of membrane potential on conductance sublevels of chloride channels activated by GABA. *Proc Biol Sci* 255, 167-172, doi:10.1098/rspb.1994.0024 (1994).

21 Birnir, B., Everitt, A. B. & Gage, P. W. Characteristics of GABAA channels in rat dentate gyrus. *J Membr Biol* 142, 93-102 (1994).

22 Xin, Y. et al. RNA Sequencing of Single Human Islet Cells Reveals Type 2 Diabetes Genes. *Cell Metab* 24, 608-615, doi:51550-4131(16)30434-X [pii] 10.1016/j.cmet.2016.08.018 (2016).

23 Segerstolpe, A. et al. Single-Cell Transcriptome Profiling of Human Pancreatic Islets in Health and Type 2 Diabetes. *Cell Metab* 24, 593-607, doi:51550-4131(16)30436-3 [pii] 10.1016/j.cmet.2016.08.020 (2016).

24 Gandasi, N. R. & Barg, S. Contact-induced clustering of syntaxin and munc18 docks secretory granules at the exocytosis site. *Nat Commun* 5, 3914, doi:ncomms4914 [pii] 10.1038/ncomms4914 (2014).

25 Tsuboi, T. & Rutter, G. A. Multiple forms of "kiss-and-run" exocytosis revealed by evanescent wave microscopy. *Curr Biol* 13, 563-567, doi:S0960982203001763 [pii] (2003).

26 Gandasi, N. R. et al. Survey of Red Fluorescence Proteins as Markers for Secretory Granule Exocytosis. *PLoS One* 10, e0127801, doi:10.1371/journal.pone.0127801 PONE-D-15-03957 [pii] (2015).

27 Sieghart, W. Allosteric modulation of GABAA receptors via multiple drug-binding sites. *Adv Pharmacol* 72, 53-96, doi:51054-3589(14)00037-4 [pii] 10.1016/bs.apha.2014.10.002 (2015).

28 Hanson, S. M., Morlock, E. V., Satyshur, K. A. & Czajkowski, C. Structural requirements for eszopiclone and zolpidem binding to the gamma-aminobutyric acid type-A (GABAA) receptor are different. *J Med Chem* 51, 7243-7252, doi:10.1021/jm800889m (2008).

29 Jones, M. V. & Westbrook, G. L. Desensitized states prolong GABAA channel responses to brief agonist pulses. *Neuron* 15, 181-191, doi:0896-6273(95)90075-6 [pii] (1995).

30 Lindquist, C. E., Laver, D. R. & Birnir, B. The mechanism of SR95531 inhibition at GABA receptors examined in human alpha1beta1 and alpha1beta1gamma2S receptors. *J Neurochem* 94, 491-501, doi:JNC3240 [pii] 10.1111/j.1471-4159.2005.03240.x (2005).

31 Wlodarczyk, A. I. et al. GABA-independent GABAA receptor openings maintain tonic currents. *J Neurosci* 33, 3905-3914, doi:33/9/3905 [pii] 10.1523/JNEUROSCI.4193-12.2013 (2013).

32 Fred, R. G., Bang-Berthelsen, C. H., Mandrup-Poulsen, T., Grunnet, L. G. & Welsh, N. High glucose suppresses human islet insulin biosynthesis by inducing miR-133a leading to decreased polypyrimidine tract binding protein-expression. *PLoS One* 5, e10843, doi:10.1371/journal.pone.0010843 (2010).

33 Jin, Z., Jin, Y. & Birnir, B. GABA-activated single-channel and tonic currents in rat brain slices. *J Vis Exp*, doi:2858 [pii] 10.3791/2858 (2011).

34 Eghbali, M., Curmi, J. P., Birnir, B. & Gage, P. W. Hippocampal GABA(A) channel conductance increased by diazepam. *Nature* 388, 71-75, doi:10.1038/40404 (1997).

35 Jin, Y., Korol, S. V., Jin, Z., Barg, S. & Birnir, B. In intact islets interstitial GABA activates GABA(A) receptors that generate tonic currents in alpha-cells. *PLoS One* 8, e67228, doi:10.1371/journal.pone.0067228 PONE-D-13-10264 [pii] (2013).

36 Jin, Z. et al. Selective Changes of GABA(A) Channel Subunit mRNAs in the Hippocampus and Orbitofrontal Cortex but not in Prefrontal Cortex of Human Alcoholics. *Front Cell Neurosci* 5, 30, doi:10.3389/fncel.2011.00030 (2011).

37 Xin, Y. et al. RNA Sequencing of Single Human Islet Cells Reveals Type 2 Diabetes Genes. *Cell Metab* 24, 608-615, doi:51550-4131(16)30434-X [pii] 10.1016/j.cmet.2016.08.018 (2016).

38 Segerstolpe, A. et al. Single-Cell Transcriptome Profiling of Human Pancreatic Islets in Health and Type 2 Diabetes. *Cell Metab* 24, 593-607, doi:51550-4131(16)30436-3 [pii] 10.1016/j.cmet.2016.08.020 (2016).

39 Tsuboi, T., Ravier, M. A., Parton, L. E. & Rutter, G. A. Sustained exposure to high glucose concentrations modifies glucose signaling and the mechanics of secretory vesicle fusion in primary rat pancreatic beta-cells. *Diabetes* 55, 1057-1065, doi:55/4/1057 [pii] (2006).

40 Meur, G. et al. Insulin gene mutations resulting in early-onset diabetes: marked differences in clinical presentation, metabolic status, and pathogenic effect through endoplasmic reticulum retention. *Diabetes* 59, 653-661, doi:10.2337/db09-1091 db09-1091 [pii] (2010).

41 Fehse, F., et al., Exenatide augments first- and second-phase insulin secretion in response to intravenous glucose in subjects with type 2 diabetes. J Clin Endocrinol Metab, 2005. 90(11): p. 5991-7.

42 Sosenko, J. M., et al., Acceleration of the loss of the first-phase insulin response during the progression to type 1 diabetes in diabetes prevention trial-type 1 participants. Diabetes, 2013. 62(12): p. 4179-83.

43 Caumo, A. and L. Luzi, *First-phase insulin secretion: does it exist in real life? Considerations on shape and function.* Am J Physiol Endocrinol Metab, 2004. 287(3): p. E371-85.

44 Fu, Z., E. R. Gilbert, and D. Liu, *Regulation of insulin synthesis and secretion and pancreatic Beta-cell dysfunction in diabetes.* Curr Diabetes Rev, 2013. 9(1): p. 25-53.

45 Cernea, S. and M. Dobreanu, *Diabetes and beta cell function: from mechanisms to evaluation and clinical implications.* Biochem Med (Zagreb), 2013. 23(3): p. 266-80.

46 Maganti et al. *From immunobiology to β-cell biology*, Islets, 2014; 6:e28778

American, A. D. (2017). 2. Classification and Diagnosis of Diabetes. Diabetes Care 40, S11-S24.

Baekkeskov, S., Aanstoot, H. J., Christgau, S., Reetz, A., Solimena, M., Cascalho, M., Folli, F., Richter-Olesen, H., and De Camilli, P. (1990). Identification of the 64K autoantigen in insulin-dependent diabetes as the GABA-synthesizing enzyme glutamic acid decarboxylase. Nature 347, 151-156.

Barg, S., Olofsson, C. S., Schriever-Abeln, J., Wendt, A., Gebre-Medhin, S., Renstrom, E., and Rorsman, P. (2002).

Delay between fusion pore opening and peptide release from large dense-core vesicles in neuroendocrine cells. Neuron 33, 287299.

Ben-Othman, N., Vieira, A., Courtney, M., Record, F., Gjernes, E., Avolio, F., Hadzic, B., Druelle, N., Napolitano, T., Navarro-Sanz, S., et al. (2017). Long-term GABA administration induces alpha cell-mediated beta-like cell neogenesis. Cell 168, 73-85 ell.

Birnir, B., Everitt, A. B., and Gage, P. W. (1994). Characteristics of GABAA channels in rat dentate gyrus. J Membr Biol 142, 93-102.

Bjurstom, H., Wang, J., Ericsson, I., Bengtsson, M., Liu, Y., Kumar-Mendu, S., Issazadeh-Navikas, S., and Birnir, B. (2008). GABA, a natural immunomodulator of T lymphocytes. J Neuroimmunol 205, 44-50.

Blatz, A. L., and Magleby, K. L. (1986). Correcting single-channel data for missed events. Biophys J 49, 967-980.

Braun, M., Ramracheya, R., Bengtsson, M., Clark, A., Walker, J. N., Johnson, P. R., and Rorsman, P. (2010). Gamma-aminobutyric acid (GABA) is an autocrine excitatory transmitter in human pancreatic beta-cells. Diabetes 59, 1694-1701.

Braun, M., Wendt, A., Birnir, B., Broman, J., Eliasson, L., Galvanovskis, J., Gromada, J., Mulder, H., and Rorsman, P. (2004). Regulated exocytosis of GABA-containing synaptic-like microvesicles in pancreatic beta-cells. J Gen Physiol 123, 191-204. Caicedo, A. (2013). Paracrine and autocrine interactions in the human islet: more than meets the eye. Semin Cell Dev Biol 24, 11-21.

Colquhoun, D., and Hawkes, A. G. (1981). On the stochastic properties of single ion channels. Proc R Soc Lond B Biol Sci 211, 205-235.

Colquhoun, D., and Hawkes, A. G. (1982). On the stochastic properties of bursts of single ion channel openings and of clusters of bursts. Philos Trans R Soc Lond B Biol Sci 300, 1-59.

Eghbali, M., Curmi, J. P., Birnir, B., and Gage, P. W. (1997). Hippocampal GABAA channel conductance increased by diazepam. Nature 388, 71-75.

Fiorina, P. (2013). GABAergic system in beta-cells: from autoimmunity target to regeneration tool. Diabetes 62, 3674-3676.

Fred, R. G., Bang-Berthelsen, C. H., Mandrup-Poulsen, T., Grunnet, L. G., and Welsh, N. (2010). High glucose suppresses human islet insulin biosynthesis by inducing miR-133a leading to decreased polypyrimidine tract binding protein-expression. PLoS One 5, e10843.

Gage, P. W., and Chung, S. H. (1994). Influence of membrane potential on conductance sublevels of chloride channels activated by GABA. Proc Biol Sci 255, 167-172.

Gandasi, N. R., and Barg, S. (2014). Contact-induced clustering of syntaxin and munc18 docks secretory granules at the exocytosis site. Nat Commun 5, 3914. Gilon, P., Bertrand, G., Loubatieres-Mariani, M. M., Remacle, C., and Henquin, J. C. (1991). The influence of gamma-aminobutyric acid on hormone release by the mouse and rat endocrine pancreas. Endocrinology 129, 2521-2529.

Giorda, C. B., Russo, G. T., Cercone, S., De Cosmo, S., Nicolucci, A., and Cucinotta, D. (2016). Incidence and correlated factors of beta cell failure in a 4-year follow-up of patients with type 2 diabetes: a longitudinal analysis of the BETADECLINE study. Acta Diabetol 53, 761-767.

Hamill, O. P., Marty, A., Neher, E., Sakmann, B., and Sigworth, F. J. (1981). Improved patch-clamp techniques for high-resolution current recording from cells and cell-free membrane patches. Pflugers Arch 391, 85-100.

Hanson, S. M., Morlock, E. V., Satyshur, K. A., and Czajkowski, C. (2008). Structural requirements for eszopiclone and zolpidem binding to the gamma-aminobutyric acid type-A (GABAA) receptor are different. J Med Chem 51, 7243-7252.

Hoist, J. J. (2007). The physiology of glucagon-like peptide 1. Physiol Rev 87, 1409-1439.

Jin, Y., Korol, S. V., Jin, Z., Barg, S., and Birnir, B. (2013). In intact islets interstitial GABA activates GABAA receptors that generate tonic currents in alpha-cells. PLoS One 8, e67228.

Jin, Z., Jin, Y., and Birnir, B. (2011). GABA-activated single-channel and tonic currents in rat brain slices. J Vis Exp.

Jones, M. V., and Westbrook, G. L. (1995). Desensitized states prolong GABAA channel responses to brief agonist pulses. Neuron 15, 181-191.

Kanaani, J., Cianciaruso, C., Phelps, E. A., Pasquier, M., Brioudes, E., Billestrup, N., and Baekkeskov, S. (2015). Compartmentalization of GABA synthesis by GAD67 differs between pancreatic beta cells and neurons. PLoS One 10, e0117130. Korol, S. V., Jin, Z., Babateen, O., and Birnir, B. (2015). GLP-1 and exendin-4 transiently enhance GABAA receptor-mediated synaptic and tonic currents in rat hippocampal CA3 pyramidal neurons. Diabetes 64, 79-89.

Lawlor, N., George, J., Bolisetty, M., Kursawe, R., Sun, L., Sivakamasundari, V., Kycia, I., Robson, P., and Stitzel, M. L. (2017). Single-cell transcriptomes identify human islet cell signatures and reveal cell-type-specific expression changes in type 2 diabetes. Genome Res 27, 208-222.

Li, J., Casteels, T., Frogne, T., Ingvorsen, C., Honore, C., Courtney, M., Huber, K. V., Schmitner, N., Kimmel, R. A., Romanov, R. A., et al. (2017). Artemisinins target GABAA receptor signaling and impair alpha cell identity. Cell 168, 86-100 e115.

Li, J., Zhang, Z., Liu, X., Wang, Y., Mao, F., Mao, J., Lu, X., Jiang, D., Wan, Y., Lv, J. Y., et al. (2015). Study of GABA in healthy volunteers: pharmacokinetics and pharmacodynamics. Front Pharmacol 6, 260.

Lindquist, C. E., Laver, D. R., and Birnir, B. (2005). The mechanism of SR95531 inhibition at GABA receptors examined in human a1J31 and a1J31g2S receptors. J Neurochem 94, 491-501.

Meur, G., Simon, A., Harun, N., Virally, M., Dechaume, A., Bonnefond, A., Fetita, S., Tarasov, A. I., Guillausseau, P. J., Boesgaard, T. W., et al. (2010). Insulin gene mutations resulting in early-onset diabetes: marked differences in clinical presentation, metabolic status, and pathogenic effect through endoplasmic reticulum retention. Diabetes 59, 653-661.

Neher, E., and Sakmann, B. (1976). Single-channel currents recorded from membrane of denervated frog muscle fibres. Nature 260, 799-802.

Obermuller, S., Lindqvist, A., Karanauskaite, J., Galvanovskis, J., Rorsman, P., and Barg, S. (2005). Selective nucleotide-release from dense-core granules in insulin-secreting cells. J Cell Sci 118, 4271-4282.

Olsen, R. W., and Sieghart, W. (2008). International Union of Pharmacology. LXX. Subtypes of gamma-aminobutyric acidA receptors: classification on the basis of subunit composition, pharmacology, and function. Update. Pharmacol Rev 60, 243-260.

Olsen, R. W., and Sieghart, W. (2009). GABAA receptors: subtypes provide diversity of function and pharmacology. Neuropharmacology 56, 141-148. Rodriguez-Diaz, R., and Caicedo, A. (2014). Neural control of the endocrine pancreas. Best Pract Res Clin Endocrinol Metab 28, 745-756.

Rorsman, P., and Ashcroft, F. M. (2018). Pancreatic beta-cell electrical activity and insulin secretion: of mice and men. Physiol Rev 98, 117-214.

Rorsman, P., Berggren, P. O., Bokvist, K., Ericson, H., Mohler, H., Ostenson, C. G., and Smith, P. A. (1989). Glucose-inhibition of glucagon secretion involves activation of GABAA-receptor chloride channels. Nature 341, 233-236.

Rorsman, P., and Braun, M. (2013). Regulation of insulin secretion in human pancreatic islets. Annu Rev Physiol 75, 155-179.

Segerstolpe, A., Palasantza, A., Eliasson, P., Andersson, E. M., Andreasson, A. C., Sun, X., Picelli, S., Sabirsh, A., Clausen, M., Bjursell, M. K., et al. (2016). Single-cell transcriptome profiling of human pancreatic islets in health and type 2 diabetes. Cell Metab 24, 593-607.

Sieghart, W. (2015). Allosteric modulation of GABAA receptors via multiple drug-binding sites. Adv Pharmacol 72, 53-96.

Soltani, N., Qiu, H., Aleksic, M., Glinka, Y., Zhao, F., Liu, R., Li, Y., Zhang, N., Chakrabarti, R., Ng, T., et al. (2011). GABA exerts protective and regenerative effects on islet beta cells and reverses diabetes. Proc Natl Acad Sci USA.

Taneera, J., Jin, Z., Jin, Y., Muhammed, S. J., Zhang, E., Lang, S., Salehi, A., Korsgren, O., Renstrom, E., Groop, L., et al. (2012). gamma-Aminobutyric acid (GABA) signalling in human pancreatic islets is altered in type 2 diabetes. Diabetologia 55, 1985-1994.

Tian, J., Dang, H., Chen, Z., Guan, A., Jin, Y., Atkinson, M. A., and Kaufman, D. L. (2013). gamma-Aminobutyric acid regulates both the survival and replication of human beta-cells. Diabetes 62, 3760-3765.

Tian, J., Lu, Y., Zhang, H., Chau, C. H., Dang, H. N., and Kaufman, D. L. (2004). Gamma-aminobutyric acid inhibits T cell autoimmunity and the development of inflammatory responses in a mouse type 1 diabetes model. J Immunol 173, 52985304.

Tsuboi, T., Ravier, M. A., Parton, L. E., and Rutter, G. A. (2006). Sustained exposure to high glucose concentrations modifies glucose signaling and the mechanics of secretory vesicle fusion in primary rat pancreatic beta-cells. Diabetes 55, 10571065.

Tsuboi, T., and Rutter, G. A. (2003). Multiple forms of "kiss-and-run" exocytosis revealed by evanescent wave microscopy. Curr Biol 13, 563-567.

Verdoorn, T. A., Draguhn, A., Ymer, S., Seeburg, P. H., and Sakmann, B. (1990). Functional properties of recombinant rat GABAA receptors depend upon subunit composition. Neuron 4, 919-928.

Wendt, A., Birnir, B., Buschard, K., Gromada, J., Salehi, A., Sewing, S., Rorsman, P., and Braun, M. (2004). Glucose inhibition of glucagon secretion from rat alpha-cells is mediated by GABA released from neighboring beta-cells. Diabetes 53, 1038-1045.

Xin, Y., Kim, J., Ni, M., Wei, Y., Okamoto, H., Lee, J., Adler, C., Cavino, K., Murphy, A. J., Yancopoulos, G. D., et al. (2016a). Use of the Fluidigm C1 platform for RNA sequencing of single mouse pancreatic islet cells. Proc Natl Acad Sci USA 113, 3293-3298.

Xin, Y., Kim, J., Okamoto, H., Ni, M., Wei, Y., Adler, C., Murphy, A. J., Yancopoulos, G. D., Lin, C., and Gromada, J. (2016b). RNA sequencing of single human islet cells reveals type 2 diabetes genes. Cell Metab 24, 608-615.

Xu, C., Zhang, W., Rondard, P., Pin, J. P., and Liu, J. (2014). Complex GABAB receptor complexes: how to generate multiple functionally distinct units from a single receptor. Front Pharmacol 5, 12.

WO15140081 A1

---

The invention claimed is:

1. A method comprising:
    administering a gamma-aminobutyric acid type A (GABAA) receptor agonist to a human patient having a disorder caused or influenced by dysfunction of β cells to decrease the rate of insulin granule exocytosis and increase the amount of insulin released per insulin granule exocytosis event, and
    measuring first phase insulin secretion in said human patient.

2. The method according to claim 1, wherein the GABAA receptor agonist is formulated in a controlled release composition.

3. The method according to claim 1, wherein the GABAA receptor agonist is administered in an amount effective to achieve an interstitial concentration of GABAA receptor agonist in the range of 100 to 1000 nM.

4. The method according to claim 1, wherein the GABAA receptor receptor agonist does not normally penetrate the blood brain barrier.

5. The method according to claim 1 wherein the GABAA receptor agonist is selected from the group consisting of GABA, muscimol, thiomuscimol, cis-aminocrotonic acid (CACA), homotaurine, bamaluzole, gabamide, GABOB, gaboxadol, ibotenic acid, isoguvacine, isonipecotic acid, phenibut, picamilon, progabide, quisqualamine, progabide acid (SL 75102).

6. The method according to claim 1, further comprising administering glucagon-like peptide 1 (GLP-1), a dipeptidyl peptidase 4 inhibitor (DPP4i) or a Positive Allosteric Modulator of a $GABA_A$ receptor (PAM) wherein said PAM binds to the α2, α5 β3 or γ2 $GABA_A$ receptor subunit, to said human patient.

7. The method according to claim 6, wherein GLP-1 or DPP4i is administered in an amount effective to achieve an interstitial concentration of GLP-1 that is less than 0.5% of the interstitial concentration of GABAA receptor agonist.

8. The method according to claim 6, wherein the Positive Allosteric Modulator of a GABAA receptor (PAM) is selected from the group consisting of allobarbital (5,5-diallylbarbiturate), amobarbital (5-ethyl-5-isopentyl-barbiturate), aprobarbital (5-allyl-5-isopropyl-barbiturate), alphenal (5-allyl-5-phenyl-barbiturate), barbital (5,5-diethylbarbiturate), brallobarbital (5-allyl-5-(2-bromo-allyl)-barbiturate), pentobarbital (5-ethyl-5-(1-methylbutyl)-barbiturate), phenobarbital (5-ethyl-5-phenylbarbiturate), secobarbital (5-[(2R)-pentan-2-yl]-5-prop-2-enyl-barbiturate), alprazolam, bromazepam, chlordiazepoxide, midazolam, clonazepam, clorazepate, diazepam, estazolam, flurazepam, halazepam, ketazolam, lorazepam, nitrazepam, oxazepam, prazepam, quazepam, temazepam, and triazolam.

9. The method according to claim 1, wherein the disorder caused or influenced by dysfunction of B cells is selected from presymptomatic Type 1 diabetes of stage 1, presymptomatic Type 1 diabetes of stage 2, pre-Type 2 Diabetes, impaired glucose tolerance, Type 2 Diabetes, Type 1 Diabetes, and obesity.

10. The method according to claim 1, comprising decreasing the rate of insulin granule exocytosis in said patient.

11. The method of claim 1, wherein the disorder is selected from presymptomatic Type 1 diabetes of stage 1, presymptomatic Type 1 diabetes of stage 2, pre-Type 2 Diabetes, impaired glucose tolerance, Type 2 Diabetes, Type 1 Diabetes, and obesity.

* * * * *